US008679746B2

(12) United States Patent
Nielsen et al.

(10) Patent No.: US 8,679,746 B2
(45) Date of Patent: Mar. 25, 2014

(54) COMPOSITIONS AND METHODS FOR PREDICTING OUTCOME OF TREATMENT

(75) Inventors: Kirsten Vang Nielsen, Brønshøj (DK); Bent Laursen Ejlertsen, Brønshøj (DK); Tim Svenstrup Poulsen, Hørsholm (DK); Henning T. Mouridsen, Holte (DK)

(73) Assignee: Dako Denmark A/S, Glostrup (DK)

( * ) Notice: Subject to any disclaimer, the term of this patent is extended or adjusted under 35 U.S.C. 154(b) by 959 days.

(21) Appl. No.: 11/915,970

(22) PCT Filed: May 30, 2006

(86) PCT No.: PCT/DK2006/000300
§ 371 (c)(1),
(2), (4) Date: Aug. 6, 2008

(87) PCT Pub. No.: WO2006/128463
PCT Pub. Date: Dec. 7, 2006

(65) Prior Publication Data
US 2009/0042187 A1 Feb. 12, 2009

Related U.S. Application Data

(60) Provisional application No. 60/686,070, filed on May 31, 2005.

(51) Int. Cl.
C12Q 1/68 (2006.01)
(52) U.S. Cl.
USPC .......................................................... 435/6.1
(58) Field of Classification Search
None
See application file for complete search history.

(56) References Cited

FOREIGN PATENT DOCUMENTS

EP    1 510 588 A1    3/2005

OTHER PUBLICATIONS

Kornmann et al. Clinical Cancer Research vol. 9, pp. 4116-4124, 2003.*
Affymetrix. GeneChip Human Genome U133 Set. 2001, Affymetrix, Inc. two pages.*
Affymetrix Expression Probeset Details for DHFR. Accessed from https://www.affymetrix.com/analysis/netaffx/fullrecord. affx?pk=HG-U133A%3A202533_S_AT, on Aug. 3, 2010, five pages.*
Affymetrix Expression Probeset Details for TYMS. Accessed from https://www.affymetrix.com/analysis/netaffx/fullrecord. affx?pk=HG-U133A%3A217684_AT, on Aug. 3, 2010, five pages.*
Scalon et al. (Advances in experimental medicine and biology (1988) vol. 244, pp. 127-135).*
Lonn et al. (Cancer 1996; 77:107-112).*
Wang et al. (PNAS Mar. 2, 2004, vol. 101, No. 9, pp. 3089-3094).*
Konishi (Kosankinbyo Kenkyusho Zasshi (1988), 40(3/4), 241-52.*
Horikoshi et al. (Cancer Research, 52 108-116, Jan. 1, 1992).*
Heidelberger, C. et al., "Fluorinated pyrimidines, a new class of tumour-inhibitory compounds," Nature, 179:663-666 (1957).
Greenspan, E. M. et al., "Response of advanced breast carcinoma to the combination of the antimetabolite, methotrexate, and the alkylating agent, thio-TEPA," Journal of the Mount Sinai Hospital, New York, 30:246-267 (1963).
Cooper, R. G., "Combination chemotherapy in hormone-resistant breast cancer," Proceedings of the American Association for Cancer Research, 10:15 (1969).
Chu, E. et al., "Mechanism of thymidylate synthase inhibition by methotrexate in human neoplastic cell lines and normal human myeloid progenitor cells," The Journal of Biological Chemistry, 265:8470-8478 (1990).
Gudkov, A. V. et al., "Isolation of genetic suppressor elements, inducing resistance to topoisomerase II-interactive cytotoxic drugs, from human topoisomerase II cDNA," Proceedings of the National Academy of Sciences, 90:3231-3235 (1993).
Muss, H. B. et al., "c-erbB-2 expression and response to adjuvant therapy in women with node-positive early breast cancer," The New England Journal of Medicine, 330: 1260-1266 (1994).
IMPACT (International Multicentre Pooled Analysis of Colon Cancer Trials) Investigators, "Efficacy of adjuvant fluorouracil and folinic acid in colon cancer," The Lancet, 345: 939-944 (1995).
Thorlacius, B. et al., "TP53 mutations and abnormal p53 protein staining in breast carcinomas related to prognosis," European Journal of Cancer, 31A: 1856-1861 (1995).
Fung, K. P. et al., "Human tumour necrosis factor-α inhibits glucose transport in cultured ehrlich ascites tumour cells," Life Sciences, 57:PL1-PL6 (1995).
Berger, J. M. et al., "Structure and mechanism of DNA topoisomerase II," Nature, 379:225-232 (1996).
Lönn, U. et al., "Higher frequency of gene amplification in breast cancer patients who received adjuvant chemotherapy," Cancer, 77: 107-112 (1996).
Coukell, A. J. and Faulds, D., "Epirubicin. An updated review of its pharmacodynamic and pharmacokinetic properties and therapeutic efficacy in the management of breast cancer," Drugs, 53:453-482 (1997).
Thor, A. D. et al., "erbB-2, p53, and efficacy of adjuvant therapy in lymph node-positive breast cancer," Journal of the National Cancer Institute, 90:1346-1360 (1998).
Clahsen, P. C. et al., "p53 protein accumulation and response to adjuvant chemotherapy in premenopausal women with node-negative early breast cancer," Journal of Clinical Oncology, 16:470-479 (1998).
Reed, E., "Platinum-DNA adduct, nucleotide excision repair and platinum based anti-cancer chemotherapy," Cancer Treatment Reviews, 24:331-344 (1998).
Leichman, C. G., "Thymidylate synthase as a predictor of response," Oncology, 12:43-47 (1998).
Lenz, H. J. et al., "p53 and thymidylate synthase expression in untreated stage II colon cancer: Associations with recurrence, survival and site," Clinical Cancer Research, 4:1227-1234 (1998).
EBCTCG (Early Breast Cancer Trialists' Collaborative Group), "Polychemotherapy for early breast cancer: an overview of the randomised trials," The Lancet, 352:930-942 (1998).
Ingvarsson, S., "Molecular genetics of breast cancer progression," Cancer Biology, 9:277-288 (1999).

(Continued)

Primary Examiner — Juliet Switzer
(74) Attorney, Agent, or Firm — Finnegan, Henderson, Farabow, Garrett & Dunner, L.L.P.

(57) ABSTRACT

This invention is directed to compositions and their uses for detection of markers. Such markers may be useful in the understanding of the underlying molecular event leading to a condition or a disease in a subject. These markers may also be useful for characterization of neoplastic cells and cancer cells and their response to certain therapeutical regimes. Therefore the invention as disclosed may contribute to the improvement of the stratification of patients for the best possible treatment.

5 Claims, 8 Drawing Sheets

(56) References Cited

OTHER PUBLICATIONS

Mouridsen, H. T. et al., "Adjuvant anthracycline in breast cancer. Improved outcome in premenopausal patients following substitution of methotrexate in the CMF combination with epirubicin," Abstract in *Proceedings of the American Society of Clinical Oncology*, 18:68a (1999).

Jiang, H. and Yang, L. Y., "Cell cycle checkpoint abrogator UCN-01 inhibits DNA repair: Association with attenuation of the interaction of XPA and ERCC1 nucleotide excision repair proteins," *Cancer Research*, 59:4529-4534 (1999).

Ormrod, D. et al., "Epirubicin. A review of its efficacy as adjuvant therapy and in the treatment of metastatic disease in breast cancer," *Drugs & Aging*, 15:389-416 (1999).

Schüller, J. et al., "Preferential activation of capecitabine in tumor following oral administration to colorectal cancer patients," *Cancer Chemotherapy and Pharmacology*, 45:291-297 (2000).

Salonga, D. et al., "Colorectal tumors responding to 5-fluorouracil have low gene expression levels of dihydropyrimidine dehydrogenase, thymidylate synthase, and thymidine phosphorylase," *Clinical Cancer Research*, 6:1322-1327 (2000).

Overgaard, J. et al., "TP53 mutation is an independent prognostic marker for poor outcome in both node-negative and node-positive breast cancer," *Acta Oncologica*, 39:327-333 (2000).

Paik, S. et al., "HER2 and choice of adjuvant chemotherapy for invasive breast cancer: national surgical adjuvant breast and bowel project protocol B-15," *Journal of the National Cancer Institute*, 92:1991-1998 (2000).

Järvinen, T. A. H. et al., "Amplification and deletion of topoisomerase IIα associate with erbB-2 amplification and affect sensitivity to topoisomerase II inhibitor doxorubicin in breast cancer," *American Journal of Pathology*, 156:839-847 (2000).

Paradiso, A. et al., "Thymidilate synthase and p53 primary tumour expression as predictive factors for advanced colorectal cancer patients," *British Journal of Cancer*, 82:560-567 (2000).

Takenoue, T. et al., "Relation between thymidylate synthase expression and survival in colon carcinoma, and determination of appropriate application of 5-fluorouracil by immunohistochemical method," *Annals of Surgical Oncology*, 7:193-198 (2000).

Geisler, S. et al., "Influence of TP53 gene alterations and c-erbB-2 expression on the response to treatment with Doxorubicin in locally advanced breast cancer," *Cancer Research*, 61:2505-2512 (2001).

Di Leo, A. et al., "HER-2 and topo-isomerase IIα as predictive markers in a population of node-positive breast cancer patients randomly treated with adjuvant CMF or epirubicin plus cyclophosphamide," *Annals of Oncology*, 12:1081-1089 (2001).

Harris, L. N. et al., "Induction of topoisomerase II activity after erbB2 activation is associated with a differential response to breast cancer chemotherapy," *Clinical Cancer Research*, 7:1497-1504 (2001).

Watanabe, T. et al., "Molecular predictors of survival after adjuvant chemotherapy for colon cancer," *The New England Journal of Medicine*, 344:1196-1206 (2001).

Iacopetta, B. et al., "A polymorphism in the enhancer region of the thymidylate synthase promoter influences the survival of colorectal cancer patients treated with 5-fluorouracil," *British Journal of Cancer*, 85:827-830 (2001).

Park, S. et al., "Identification of signature genes associated with 5-fluorouracil-resistance in human gastric cancer cells," *Biotechnology Letters*, 24:1651-1657 (2002).

Coon, J. S. et al., "Amplification and overexpression of topoisomerase IIα predict response to anthracycline-based therapy in locally advanced breast cancer," *Clinical Cancer Research*, 8:1061-1067 (2002).

Di Leo, A. et al., "HER-2 amplification and topoisomerase IIα gene aberrations as predictive markers in node-positive breast cancer patients randomly treated either with an anthracycline-based therapy or with cyclophosphamide, methotrexate, and 5-fluorouracil," *Clinical Cancer Research*, 8:1107-1116 (2002).

Edler, D. et al., "Thymidylate synthase expression in colorectal cancer: A prognostic and predictive marker of benefit from adjuvant fluorouracil-based chemotherapy," *Journal of Clinical Oncology*, 20:1721-1728 (2002).

Banderjee, D. et al., "Novel aspects of resistance to drugs targeted to dihydrofolate reductase and thymidylate synthase," *Biochimica et Biophysica Acta*, 1587:164-173 (2002).

Malet-Martino, M. et al., "The prodrugs of 5-fluorouracil," *Current Medicinal Chemistry—Anticancer Agents*, 2:267-310 (2002).

Kornmann, M. et al., "Thymidylate synthase and dihydropyrimidine dehydrogenase mRNA expression levels: Predictors for survival in colorectal cancer patients receiving adjuvant 5-fluorouracil," *Clinical Cancer Research*, 9:4116-4124 (2003).

Mariadason, J. M. et al., "Gene expression profiling-based prediction of response of colon carcinoma cells to 5-fluorouracil and camptothecin," *Cancer Research*, 63:8791-8812 (2003).

Maxwell, P. J. et al., "Identification of 5-fluorouracil-inducible target genes using cDNA microarray profiling," *Cancer Research*, 63:4602-4606 (2003).

Park, K. et al., "Topoisomerase II-α (topoII) and HER2 amplification in breast cancers and response to preoperative doxorubicin chemotherapy," *European Journal of Cancer*, 39:631-634 (2003).

Allegra, C. J. et al., "Prognostic value of thymidylate synthase, Ki-67, and p53 in patients with Dukes' B and C colon cancer: A National Cancer Institute-National Surgical Adjuvant Breast and Bowel Project collaborative study," *Journal of Clinical Oncology*, 21:241-250 (2003).

Wang, T. et al., "Digital karyotyping identifies thymidylate synthase amplification as a mechanism of resistance to 5-fluorouracil in metastatic colorectal cancer patients," *Proceedings of the National Academy of Sciences*, 101:3089-3094 (2004).

Patel, A. et al., "Enzyme expression profiles suggest the novel tumor-activated fluoropyrimidine carbamate capecitabine (Xeloda) might be effective against papillary thyroid cancers of children and young adults," *Cancer Chemotherapy and Pharmacology*, 53:409-414 (2004).

EBCTCG (Early Breast Cancer Trialists' Collaborative Group), "Effects of chemotherapy and hormonal therapy for early breast cancer on recurrence and 15-year survival: an overview of the randomised trials," *The Lancet*, 365:1687-1717 (2005).

Kidd, E. A. et al., "Variance in the expression of 5-fluorouracil pathway genes in colorectal cancer," *Clinical Cancer Research*, 11:2612-2619 (2005).

Knoop, A. S. et al., "Retrospective analysis of topoisomerase IIα amplifications and deletions as predictive markers in primary breast cancer patients randomly assigned to cyclophosphamide, methotrexate, and fluorouracil or cyclophosphamide, epirubicin, and fluorouracil: Danish Breast Cancer Cooperative Group," *Journal of Clinical Oncology*, 23:7483-7490 (2005).

International Search Report for PCT/DK2006/000300 mailed Aug. 11, 2006.

\* cited by examiner

FIGURE 3

| Clone | Length (kb) | Start (base no.) | End (base no.) | Clone | Length (kb) | Start (base no.) | End (base no.) |
|---|---|---|---|---|---|---|---|
| TYMS | | | | TP | | | |
| 18p11,32 | 15.9 | 663,497 | 647,622 | 22q13,33 | 4.2 | 49,258,572 | 49,254,327 |
| RP11-145B19 | 163.9 | 522,097 | 686,036 | CTD-2552O4 | 173.1 | 49,112,016 | 49,285,072 |
| RP11-381D10 | 173.8 | 611,361 | 785,199 | RP4-579N16 | 106.7 | 49,153,144 | 49,259,882 |
| RP11-806L2 | 203.7 | 511,332 | 715,019 | CIT987SK-384D8 | 138.9 | 49,229,925 | 49,368,773 |
| RP11-904F1 | 205.4 | 700,619 | 906,050 | | | | |
| DHFR | | | | DPD | | | |
| 5q14,1 | 27.8 | 79,958,449 | 79,986,119 | 1p21,3 | 843.3 | 97,255,322 | 98,098,600 |
| RP11-643F22 | 198.1 | 79,882,591 | 80,079,121 | CTD-2601E23 | 211.0 | 97,263,564 | 97,474,536 |
| RP11-90A4 | 180.5 | 79,882,591 | 80,063,088 | RP11-595B14 | 193.4 | 97,474,544 | 97,668,332 |
| RP11-957J15 | 197.0 | 79,731,156 | 79,927,638 | RP11-373P8 | 167.4 | 97,668,368 | 97,835,711 |
| RP11-120L6 | 160.5 | 79,915,645 | 80,076,177 | RP11-134M5 | 161.6 | 97,835,721 | 97,997,335 |
| | | | | CTD-2590D17 | 221.7 | 97,456,343 | 97,678,022 |

FIGURE 4

| Assay | Target sequence | Length | Clones / location |
|---|---|---|---|
| TYMS | Centromere 18 | 1.7kb | 2xBA |
| DHFR | 5p12 | 561kb | RP11-671H24, 929P16, and 81G1 |
| TP | 22q11 | 408kb | Telomeric to the BCR breakpoint* |
| DPD | 1p32 | 566kb | Telomeric to the TAL1 gene** |

\*　　This probe is part of the BCR FISH split signal probes (Y5403).
\*\*　This probe is part of the SIL-TAL1 FISH split signal probes (Y5405).

COMPOSITIONS AND METHODS FOR PREDICTING OUTCOME OF TREATMENT

This application is a national stage filing under 35 U.S.C. §371 of International Application No. PCT/DK2006/000300 filed on 30 May 2006. This application claims the benefit of priority of U.S. Provisional Application No. 60/686,070, filed on 31 May 2005.

TECHNICAL FIELD

The invention pertains to the field of molecular biology and protein chemistry. More specifically the invention pertains to compositions, methods and kits for detection of markers that may be useful for stratification of patients for the best possible treatment.

BACKGROUND OF THE INVENTION

Each cancer patient is unique, as is the tumor and the cancer. The course of the disease and the effect of therapy are a product of the genetics and the environment of both the patient and the tumor. Through tailoring of chemotherapy to the specific genetic profile of the patient and the tumor, pharmacogenetics may potentially increase the efficacy, lessen the toxicity and decrease the overall costs of chemotherapy. At the cellular level cancer is a genetic disease and progression of the tumor is associated with a progressively larger number of genetic changes, e.g. translocations, amplifications, deletions and mutations. The genes involved in the cancerous process are oncogenes and tumor suppressor genes. Oncogenes are activated through translocations and amplifications while tumor suppressor genes are eliminated primarily through mutation and deletions.

The Burden of Cancer

Based on 1998-2000 data from the Surveillance, Epidemiology, and End Results (SEER) program it have been demonstrated that the lifetime risk of developing cancer is 1 in 3 for females and 1 in 2 for males (Http://www.seer.cancer.gov). The 5-year relative survival rate varies considerably by cancer site and stage at diagnosis. Significant decreases in death rates have been observed for cancer at all sites combined, for female breast cancer and colorectal cancer of both sexes. The three most frequent cancers occurring in females are breast, lung and colon cancer, compared to males where prostate, lung and colon cancer are the most frequent. It can also be estimated that close to 10 million people in the U.S. are alive after being diagnosed with cancer. Over 2 million women who have had a previous diagnosis of breast cancer are alive today, reflecting both the high incidence and the relatively good survival of breast cancer.

The Contribution of Cytotoxic Chemotherapy to Survival of Cancer Patients

Treatment with cytotoxic agents is a well-established standard for most advanced cancers and is also increasingly becoming an integrated part of treatment in primary and early cancers, examples being colorectal and breast cancers. Cytotoxic chemotherapy can in early cancers be given before surgery and radiotherapy as the primary treatment, concomitant with local therapy or adjuvant to local therapies. DNA synthesis inhibitors as 5-Fluorouracil (5-FU) have demonstrated activity in a range of advanced cancers, including colorectal, breast, and head & neck cancers. The greatest impact is however achieved in patients with operable colorectal and breast cancer were treatment with 5-FU containing chemotherapy significantly reduces the risk of recurrence and mortality (IMPACT Lancet 1995; 345:939-44, EBCTCG Lancet 2005).

The Example of Breast Cancer

Patients with primary breast cancer will often receive a complex therapy integrating multiple modalities. The local therapy may be surgery alone or a combination of surgery and radiotherapy. Systemic therapies will be advised to the majority of patients depending on characteristics of the patient and the tumor. Survival is at least as good with pre- as with postoperative chemotherapy, but the different treatment modalities are primarily given in sequence to avoid a possible interaction between different modalities.

The somatic genetic alterations involved in the etiology of breast cancer are complex and heterogeneous. Several proto-oncogenes known to be activated include MYC, ERBB2 (HER2), and CCND1 [S Ingvarsson 1999]. Activation of these genes often involves genetic aberrations such as e.g. amplification and/or translocation of the corresponding chromosomal regions, and e.g. mutations and deletions of tumor suppressor genes, such as TP53, CDH1 (encoding E-cadherin) and FHIT, have also been demonstrated. ERBB2 overexpression is observed in 20-30% of breast cancers and in general ERBB2 over expression is associated with poor prognosis. However, there are also data from retrospective studies indicating that the ERBB2 status might be of predictive value as well. TP53 mutation is observed in about 25% of breast cancers. Studies evaluating the prognostic (and predictive) value of p53 using immunohistochemical methods to determine p53 status are conflicting. However, detection of TP53 gene alterations is superior to immunostaining as a prognostic factor [S Thorlacius 1995] and TP53 mutation shows a strong association with poor prognosis [J Overgaard 2000]. It appears that TP53 mutation, or at least a subset of mutations, is also associated with resistance to anthracycline-based chemotherapy [S Geisler 2001].

Although much effort has been devoted to the study of predictive markers in cancer, only very limited details have emerged until now. In breast cancer the only predictive markers in clinical use are ER, PgR and ERBB2, predicting sensitivity to hormone and Herceptin treatment, respectively. Additional markers are in preparation for a clinical use, e.g. TOP2A copy number changes (deletion or amplification) as predictive to the outcome of anthracycline treatment. However, given the wide range of chemotherapy regimens used there is a huge need of more predictive markers to facilitate the introduction of personalized medicine.

Predictive Factors for Efficacy of Adjuvant Chemotherapy in Breast Cancer.

The efficacy of chemotherapy is well documented in early breast cancer [EBCTCG, Lancet 2005]. The first generation of clinical trials showed that chemotherapy e.g. the classical combination of Cyclophosphamid, Methotrexate and Fluorouracil (CMF) reduces the risk of recurrence and mortality of breast cancer with 20-25%. Further risk reduction has been achieved in later trials adding anthracyclines, and currently the efficacy of taxanes is being investigated. Chemotherapy is offered to a prognostic heterogeneous group of patients where the individual risk of recurrence and death from breast cancer varies from 10% to 80%. Totally, 30-40% of the expected deaths can be prevented, but in total numbers the overall survival is only reduced with a few percent (from 10% to 7%) in the low risk group, and with approximately 25% in the high-risk group (from 80% to 55%). Thus, extensive over treatment takes place with concurrent consequences in form of side effects and unintended use of resources. Therefore, a high need of development of predictive factors is present and until now unmet.

Often the mechanism of action is not known in details when a treatment is introduced in the clinical setting. A starting insight into the molecular background of the mode of action of some chemotherapeutics is emerging, and recently some examples of a relationship between the effect of treatment with a specific chemotherapy and specific genetic changes in the cancer cells has been provided. The DBCG 89-D trial showed that substitution of methotrexate in CMF with epirubicin lead to a reduction of 25% in overall survival [Mouridsen ASCO 1999]. Retrospectively it could be shown that this effect mainly is restricted to patients who harbor amplification or deletion of the TOP2A gene in their tumors [Knoop 2003]. The TOP2A gene encodes topoisomerase IIa that is the primary target of anthracyclines (e.g. epirubicin and doxorubicin).

TopoIIa is involved in DNA replication, transcription, and translation. TopoIIa introduces a temporary double DNA break, which allows the uncoiling of the DNA double helix. Following binding of epirubicin to topoIIa, the topoIIa complex is stabilized and the DNA break becomes irreversible [J M Berger 1996]. Anthracyclines are active during all phases of the cell cycle, but are most dynamic in proliferating cells [A J Coukell 1997].

In randomized trials, the survival benefit of adjuvant anthracycline-based chemotherapy seems to be restricted to ERBB2-positive patients [H B Muss 1994; A D Thor 1998; S Paik 1998; P C Clahsen 1998; S Paik 2000; A Di Leo 2001]. The gene encoding topoIIa (TOP2A) is situated close to ERBB2 and is often co-amplified with ERBB2. It has been suggested that the sensitivity to anthracycline-based chemotherapy in ERBB2-positive patients might be explained by the co-amplification of TOP2A and thereby increased expression of TopoIIa, the cellular target for anthracyclines [T A Järvinen 2000]. More recently, it has been shown that TOP2A gene copy number changes (CNC), both deletions and amplifications, are predictive to the outcome of anthracycline-based chemotherapy [Coon 2002; Di Leo 2002; Park 2003; Knoop, 2003; Harris 2004].

An important mode of action for many cytotoxic agents is the induction of DNA damage, and DNA repair can lead to general resistance. The main mode of action of Cyclophosphamide is generation of DNA cross-links that can be repaired directly or by nucleotide excision repair. Nucleotide excision repair is also central to the exchange of fluorouracil metabolites. XPD (Xeroderma Pigmentosum gene D) is involved both in the global DNA repair and the transcription dependent version of nucleotide excision repair [Reed 1998; Readon 1999] and ERCC1 (excision repair cross-complementing 1) is another critical element in this mechanism [Jiang 1999].

Thymidylate synthase (abbreviated TS for the protein and TYMS for the gene) use 5,10-Methylenetetrahydrofolat (MTHF) as a cofactor in the regulation of dTMP (thymidine monophosphat) that is critical to DNA replication and repair. The prognostic and predictive value of TS expression in tumor tissue has been the subject of numerous studies and high TS protein seems to predict resistance to TS inhibitors in patients with advanced colon cancer (Leichman 1998; Lenz 1998; Paradiso 2000). The results are less clear in the adjuvant setting where genetic markers seem to have predictive value (Watanabe 2001; Iacopetta 2001) while the IHC results are contradicting (Takenoue 2000; Edler 2002; Allegra 2003). Most likely dihydrofolate reductase (DHFR) is the main cellular target of methotrexate, and amplification of DHFR has often been correlated to resistance to both methotrexate and fluorouracil in experimental systems (Chu 1990; Banerjee 2002). The importance of thymidine phosphorylase (TP alias of ECGF1), dihydropyrimidine dehydrogenase (DPD alias of DPYD), Thymidine kinase (TK) and Methylenetetrahydrofolate reductase (MTHFR) has not yet been clarified.

DNA Synthesis Inhibitors

The synthesis and normal function of DNA and RNA is inhibited by the fluoropyrimidine 5-fluorouracil (5-FU) through inhibition of essential enzymes, primarily thymidylate synthase (TS), in the biosynthetic process and from incorporation of fluoronucleotides into the two macromolecules. Several inactive prodrugs of 5-FU have been developed, which are designed to allow intact absorption through the gastrointestinal canal and which are subsequently converted into 5-FU by metabolic transformation in the tumor or the liver. Several oral fluoropyrimidines are in development and the activity of capecitabine and UFT (uracil/Ftorafur) have been demonstrated in phase II, but results from phase III trials are awaited [M Malet-Martino 2002]. The tumor selectivity and conversion of capecitabine preferentially in tumor tissue have been demonstrated in a pharmacodynamic study, with a 3.2 fold higher FU concentration in tumor compared to normal tissue and 21 fold higher concentrations in tumor tissue compared to plasma [J Schüller 2000]. Cytotoxic chemotherapy with DNA synthesis inhibitors (as 5-FU) has demonstrated activity in a large range of malignancies and both in early and late stages of the disease. Activity has been observed both when 5-FU or analogs are given as single agents and in combinations with other agents. The importance of gene copy number changes as predictive markers has just recently been shown for Topoisomerase inhibitors. TOP2A gene copy number changes serve as an example of the importance of deletions and amplifications in predicting the outcome of anthracycline based treatment. Anthracyclines have been in clinical use since the sixties. Doxorubicin is produced by *Streptomyces*, and was in the beginning considered to be an antibiotic. Epirubicin is a semi-synthetic second-generation drug, with a more favorable therapeutic profile regarding cardio toxicity, stomatitis, and thrombopenia [D Ormrod 1999]. After 30 years of clinical use it became clear in the early nineties, that an inhibition of topoisomerase IIa protein (topoIIa) is the primary cytotoxic action of the anthracyclines [A V Gudkov 1993]. TopoIIa is involved in DNA replication, transcription, and translation. TopoIIa introduces a temporary double DNA break, which allows the uncoiling of the DNA double helix. Following binding of epirubicin to topoIIa, the topoIIa complex is stabilized and the DNA break becomes irreversible [J M Berger 1996]. Anthracyclines are active during all phases of the cell cycle, but are most dynamic in proliferating cells [A J Coukell 1997].

Drugs such as e.g. 5-Fluorouracil (5-FU) and Methotrexate interfere with key enzymatic steps in the nucleic acid syntheses. They inhibit essential biosynthetic processes and are incorporated into macromolecules such as DNA and RNA and thereby disrupt their normal function. 5-FU was introduced in 1957 and is still part of the most widely used drugs in adjuvant treatment of breast- and colon cancer. The first combination chemotherapy regimens for advanced breast cancer included antimetabolites and were introduced more than four decades ago [E M Greenspan 1963]. Following the early results of a randomized trial in advanced breast cancer [R G Cooper ASCO 1969; 10] methotrexate (MTX) and 5-FU were included in several later adjuvant trials [EBCTCG 1998].

The antimetabolites are early examples of rationally designed anticancer agents [C Heidelberger 1957]. The predominant view on the primary cellular action target of MTX is dihydrofolate reductase enzyme, and amplification of DHFR is one of the most common forms of methotrexate resistance observed in experimental systems [E Chu 1990]. Amplification of DHFR has also been associated with resistance to 5-FU in experimental systems [D Banerjee 2002]. Another potential explanation for the effect of MTX is inhibition of essential parts of the glucose transport mechanisms [K P Fung 1995].

The primary indications for use of 5-FU further to breast cancer are lung, prostate, colorectal, head & neck, pancreas, bladder, stomach, esophagus and liver.

The classification of tumors was until a decade ago often solitarily based on histology and more recently immunohistochemistry has been added. The staining pattern is however insufficient to reflect the underlying multiple molecular events characterizing the cancer cells viewed under the microscope. By surveying thousands of genes at once, using DNA arrays, it is possible to address the individual signature of every single tumor.

To improve the stratification of patients for the best treatment it would be of great benefit to the patient to select factors, which may predict the response of specific chemotherapeutic treatments. One therapeutic drug that is widely used in breast cancer as well as other types of cancer is 5-fluorouracil (5-FU).

It is thus highly desirable in the light of the aforementioned problems to develop means and methods for analyzing a patients ability to respond to a specific chemotherapeutic treatment, such as 5-FU-treatment, to increase the cancer patients wellbeing and to avoid unpleasant side effects in said cancer patients, such as e.g. breast cancer patients. Also, there is a need for identification of patients with tumors resistant to 5-FU treatment before the initiation of therapy, to avoid unpleasant side effects of said 5-FU treatment. In this respect, the present invention addresses those needs and interests.

BRIEF SUMMARY OF THE INVENTION

In a first aspect, the present invention relates to a composition comprising at least two probes binding to at least two markers from the 5-FU pathway.

In a second aspect, the present invention relates to a method for determining the level of at least two markers from the 5-FU pathway in an isolated sample from a subject by an analysis, comprising the steps: a) detecting a signal from each of at least two markers from the 5-FU pathway in said isolated sample using at least two probes binding to the at least two markers from the 5-FU pathway; b) determining the level based on the at least two signals detected.

In a third aspect, the present invention relates to use of the composition for determining the level of at least two markers selected from the 5-FU pathway in an isolated sample from a subject.

In a fourth aspect, the present invention relates to a kit for determining the level of at least two markers from the 5-FU pathway in an isolated sample from a subject by an analysis, the kit comprising: a) a composition comprising at least two probes binding to at least two markers from the 5-FU pathway; and b) instructions for using the composition.

In a fifth aspect, the present invention relates to a composition comprising at least one DNA probe binding to at least one marker from the 5-FU pathway.

In a sixth aspect, the present invention relates to a method for determining the level of at least one marker from the 5-FU pathway in an isolated sample from a subject by an analysis, comprising the steps: a) detecting a signal from at least one marker from the 5-FU pathway in said isolated sample using at least one DNA probe binding to the at least one marker from the 5-FU pathway; b) determining the level based on the at least one signal detected.

In a seventh aspect, the present invention relates to use of the composition comprising at least one DNA probe for determining the level of at least one marker selected from the 5-FU pathway in an isolated sample from a subject.

In a eight aspect, the present invention relates to a kit for determining the level of at least one marker from the 5-FU pathway in an isolated sample from a subject by an analysis, the kit comprising: a) a composition comprising at least one DNA probe binding to at least one marker from the 5-FU pathway; and b) instructions for using the composition.

In a ninth aspect, the present invention relates to a composition comprising at least one probe binding to at least one marker from the 5-FU pathway and at least one probe binding to a reference marker, wherein at least one of said probes is a DNA probe.

In a tenth aspect, the present invention relates to a method for determining the level of at least one marker from the 5-FU pathway in an isolated sample from a subject by an analysis, comprising the steps: a) detecting a signal from at least one marker from the 5-FU pathway using at least one probe binding to the at least one marker from the 5-FU pathway; b) detecting a signal from at least one reference marker using at least one probe binding to the at least one reference marker, wherein one of said probes is a DNA probe; c) determining the level of said at least one marker from the 5-FU pathway based on correlation of a signal from said at least one marker from the 5-FU pathway and a signal from said at least one reference marker.

In an eleventh aspect, the present invention relates to use of the composition comprising at least one probe for determining the level of at least one marker selected from the 5-FU pathway and at least one probe for determining the level of at least one reference marker in an isolated sample from a subject, wherein one of said probes is a DNA probe.

In a twelfth aspect, the present invention relates to a kit for determining the level of at least one marker from the 5-FU pathway in an isolated sample from a subject by an analysis, the kit comprising: a) a composition comprising at least one probe binding to at least one marker from the 5-FU pathway and at least one probe binding to a reference marker, wherein one of said probes is a DNA probe; and b) instructions for using the composition.

In particular, the level of marker to de determined is indicative of a chromosome aberration such as a deletion or amplification.

BRIEF DESCRIPTION OF THE DRAWING(S)

The invention is explained in detail below with reference to the drawing(s), in which FIG. 1 illustrates the 5-FU metabolism. a shows the 5-FU pathway, and b shows a simplified overview of 4 selected markers for 5-FU sensitivity detection.

FIG. 3 illustrates the clones selected for FISH-detection of gene aberrations.

FIG. 4 illustrates the reference probes. TP and DPD reference probes can be found in the Dako catalogue.

DETAILED DESCRIPTION OF THE INVENTION

Figure 1:
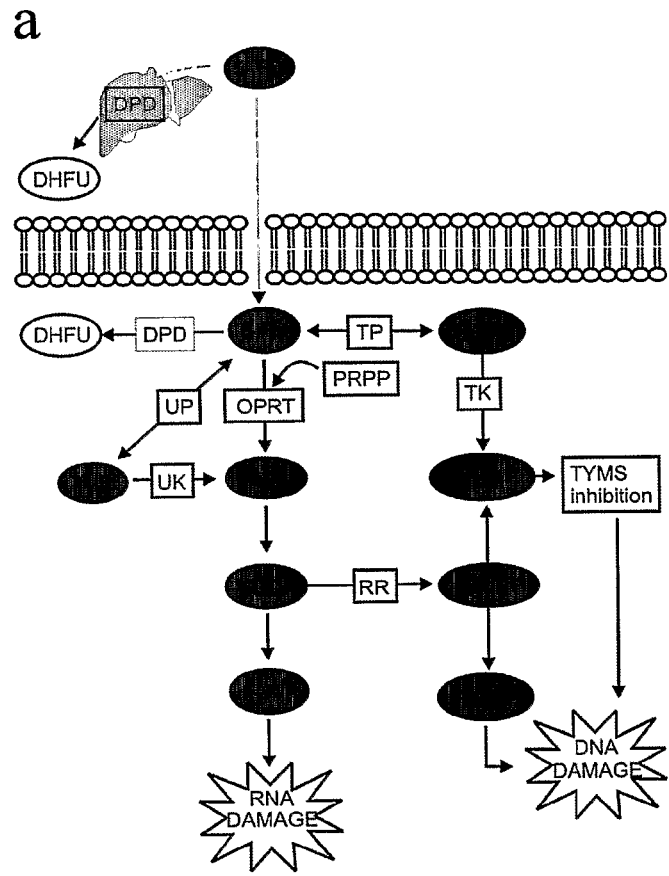
Figure 1:
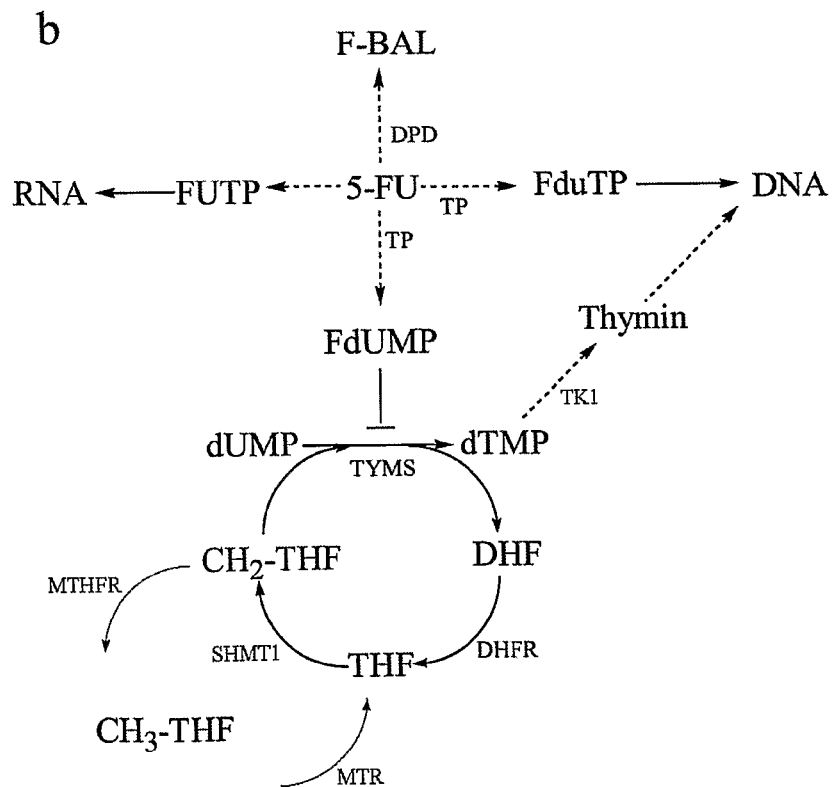
Figure 2:
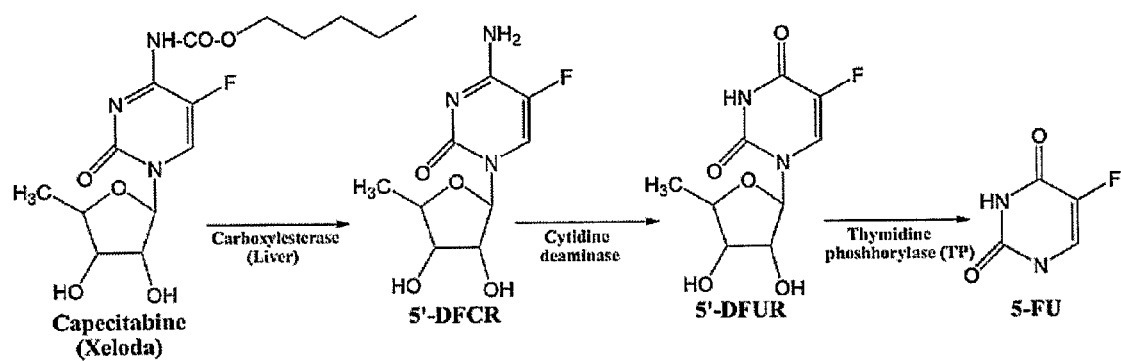
FIG. 2 illustrates the metabolic pathways from Xeloda to 5-FU and the structure of 5-FU.

The present invention is described in detail below. For the purposes of interpreting this specification the following definitions shall apply and whenever appropriate, terms used in the singular shall also include the plural and vice versa.
Definitions "Marker" as used herein, means any molecule that can be used to identify other molecules bearing complementary sequences or structures.

"5-FU pathway marker" as used herein, means any marker involved the sequence of chemical reactions affecting 5-FU metabolism involved when treating a subject with 5-Fluorouracil (5-FU).

"Reference marker" as used herein, means any marker that is not identical with the marker of interest.

"Probe" as used herein means any molecule or composition of molecules that may bind to a marker or the region(s) to be detected or visualized.

"Blocking probe" as used herein, means any probe capable of blocking, suppressing or preventing the interaction of a marker with other probes or molecules.

"Randomly distributed repeat sequence" as used herein, means any repeat sequences that occur randomly within all, or essentially all, genomic nucleic acids of an organism.

"Nucleic acid" as used herein, means any molecule of a naturally occurring nucleobase sequence-containing oligomer, polymer, or polymer segment, having a backbone formed solely from nucleotides, or analogs thereof.

"Nucleic acid analogue" as used herein, means any molecule that is not a naturally occurring nucleic acid molecule or is composed of at least one modified nucleotide, or subunit derived directly from a modification of a nucleotide.

"Nucleotide" as used herein, means any of several compounds that consist of a ribose or deoxyribose sugar joined to a purine or pyrimidine base and to a phosphate group. Nucleotides are the basic structural subunits of nucleic acids.

"Non-coding region" as used herein, means any chromosomal region not encoding a gene product.

"Gene aberration" as used herein, means any changes in the DNA.

"Detectable entity" as used herein, means any molecule or any complex of molecules that are detectable.

"Gene copy number" as used herein, means the number of a gene or part of a gene pre-sent on a chromosome. If a gene or a part of a gene is amplified, it may be found in two or more copies one the same chromosome or another chromosome.

"Gene Analysis" as used herein, means any analysis that may be suitable for analyzing genes.

"Level" as used herein, means determining whether the probe binds in such a way to indicate a normal or abnormal gene copy number.

"CMF treatment" as used herein, means a treatment using Cyclophosphamide, methotrexate and 5-fluorouracil either simultaneously or sequentially.

"Subject" as used herein, means any mammal including human having or suspected of having a disease.

"Signal" as used herein, means any form of noticeable and distinguishable information collected from visualization of the marker and reference marker.

"At least one" as used herein means one or more, i.e. 1, 2, 3, 4, 5, 6, 7, 8, 9 etc.

As revealed above, genomic, transcriptional and translational changes are known to occur upon cancer development. Gains and losses on the genomic level can result in both high and low gene expression and protein levels, where both cases can result in reduced sensitivity. The present invention discloses that determination of gene aberrations such as gene copy number changes in particular genes will, surprisingly, lead to a more precise prediction of the effect of 5-FU treatment.

In one embodiment of the compositions as defined above, the probes are nucleic acid probes, nucleic acid analogue probes or a combination of such. In another embodiment, the probes are DNA probes, PNA probes or a combination of such. Each probe may be composed of DNA probes, PNA probes or a combination thereof.

The 5-FU pathway is illustrated schematically in FIG. 1. Part a shows the structure of 5-fluorouracil (5-FU) and its degradation into non-toxic dihydrofluorouracil (DHFU) by dihydropyrimidine dehydrogenase (DPD), both occurring in the liver and inside the cancer cell. The three main active metabolites are fluorodeoxyuridine monophosphate (FdUMP), fluorodeoxyuridine triphosphate (FdUTP) and fluorouridine triphosphate (FUTP). One mechanism of 5-FU activation is conversion to fluorouridine monophosphate (FUMP), either directly by orotate phosphoribosyltransferase (OPRT) with phosphoribosyl pyrophosphate (PRPP) as cofactor, or indirectly via fluorouridine (FUR) through the sequential action of uridine phosphorylase (UP) and uridine kinase (UK). FUMP is then phosphorylated to fluorouridine diphosphate (FUDP), which can be either further phosphorylated to FUTP, or converted to fluorodeoxyuridine diphosphate (FdUDP) by ribonucleotide reductase (RR). In turn, FdUDP can either be phosphorylated or dephosphorylated to generate the active metabolites FdUTP for DNA incorporation and FdUMP for thymidylate synthase (TYMS) inhibition, respectively. Another activation pathway involves the thymidine phosphorylase (TP) catalyzed conversion of 5-FU to fluorodeoxyuridine (FUDR), which is then phosphorylated by thymidine kinase (TK) to FdUMP [Longley 2003]. Part b shows a simplified overview of the 4 selected markers for 5-FU sensitivity detection, and clarifies the details of TYMS inhibition, where deoxyuridine monophosphate (dUMP) is not converted into deoxythymine monophosphate (dTMP) upon FdUMP inhibition, and therefore no deoxythymine triphosphate (dTTP) is formed for the DNA replication and repair. Reduced folate in the form of 5,10-methylene tetrahydrofolate (CH$_2$-THF) is the methyl donor TYMS, and dihydrofolate reductase (DHFR) catalyzes part of the reduction process. Adapted from [Peters 2002].

Nucleic acid probes may be made up of naturally occurring nucleic acid molecules, such as oligodeoxynucleic acids (e.g. DNA), oligoribonucleic acids (e.g. RNA, mRNA, siRNA), and fragments thereof. Nucleic acid analogue probes may bind to the same marker as the nucleic acid probes and may be made from modified naturally occurring nucleic acid molecules or may be synthetic molecules. Non-limiting examples of a modified naturally occurring molecule is Locked Nucleic Acid (LNA), and examples of synthetic molecules may be polyamide based molecules such as e.g. Peptide Nucleic Acid (PNA), or other nucleic acid analogs or nucleic acid mimics.

Nucleic acid probes may have any length suitable for detecting the target. Usually a probe is made up of smaller fragments of varying sizes (e.g. about 50 bp to about 500 bp each) such that the probe will in total span about 30 kb to about 2 Mb. The probe will usually comprise both unique fragments as well as repeated fragments. Such repeated fragments can e.g. be removed or be blocked.

Nucleic acid analogue probes, like PNA probes, are shorter, well defined probes, typically comprising from about 10 to 25 nucleobases. A PNA probe is usually composed of several individual probes, each having 10 to 25 nucleobase units.

The probes may also be protein probes made from protein molecules such as e.g. antibodies, receptors, ligands, growth factors, DNA binding proteins or any other protein that may bind a marker of interest. The nucleic acid probe, the nucleic acid analogue probe and the protein probe may be employed in separate analyses or in combination in the same analysis. A non-limiting example could be the employment of two nucleic acid probes for detection of the marker of interest and the employment of either a nucleic acid analogue probe or a protein probe for detection of the reference marker.

Labeling of the probes may be done with different methods by means of e.g. enzymatic or chemical processes. Any labeling method known to those in the art can be used for labeling probes as used in this invention.

The marker may be a gene, fragment of a gene, including fused or overlapping fragments of a gene, or a gene with flanking regions, where the flanking regions are DNA sequences extending on either side of a specific locus or gene. Such flanking regions may for example be about 500,000 bp on each side of the gene. An example of clones for the TYMS marker comprising about 500,000 bp flanking regions are: CTD-2304H22; RP11-841C6; RP11-464L8; RP11-631M21; CTD-2573M23; CTD-3162G8G8; CTD-3232F7; RP11-170J2; RP11-252G7; RP11-699P24; RP11-805B24; CTD-3237F7; RP11-230P17; CTD-2359H18; RP11-1120H10; CTD-2509F1; RP11-431C15; RP11-361O6; RP11-1066C16; CTD-2359H18; RP11-1066G14; RP11-1034P14; RP11-1034P22; CTD-3114P12; RP11-787A12; RP11-787C12; CTD-3149J12; RP11-195P12; CTD-2595P20; CTD-2168E8; RP11-621G7; CTD-3023M8; RP11-748B19; CTD-2064P19; RP11-461K16; RP11-630F5; CTD-3021E11; CTD-3028I7; RP11-1021K17; RP11-729G15; RP11-104I5; RP11-595D13; RP11-436O7; CTD-2646F10; RP11-104A15; CTD-2024F12; CTD-2169M24; RP11-140D22; RP11-848A7; CTD-2060D6; CTD-2298K5; CTD-3022J6; RP11-29P22; RP11-790O10; RP11-89P6; RP11-91I8; RP11-694N4; RP11-752I11; RP11-324G2; CTA-186D6; RP11-88C10; RP11-608N7; RP11-732L14; RP11-324G2; RP11-705O1; RP11-839O23; RP11-683J11; RP11-815L4; RP11-720L2; RP11-179K3; RP11-778P8; RP11-823F8; RP11-791M5; RP11-672L10; RP11-827M19; RP11-19J12; RP11-607C2; RP11-267C19; CTD-3214N24; RP11-1035E2; CTD-2004F18; CTD-3155L20; CTD-2281A22; CTD-3231L23; CTD-2014P18; RP11-1150C18; RP11-170J1; CTC-790I9; RP11-76H24; RP11-48I21; CTC-775A10; CTD-2034O18; RP11-431C11; RP11-50C2; CTD-2208G7; CTD-2345G8; RP11-797C9; RP11-133D9; RP11-655D4; RP11-14P20; RP11-103B23; RP11-806L2; RP11-145B19; CTD-2593J12; CTD-3215I7; RP11-381D10; RP11-769O8; RP11-95H4; RP11-552E8; RP11-914P23; RP11-904F1; RP11-164C14; CTD-3040A20; RP11-1152E8; CTD-3065D24; CTD-3243B17; CTD-3243D18; CTD-3243D19; CTD-3113H2; RP11-1120E20; CTD-3046I16; RP11-635J20; RP11-114M20; RP11-1018M4; CTA-344N3; RP11-137K7; RP11-689C9; RP11-1005B18; RP11-126M20; CTD-2134I3; RP11-701F4; CTD-3236J23; CTD3047L19; CTD-3240G16; CTD-3148N6; RP11-22J24; RP11-1094D2; CTD-2182K19; RP11-107A13; RP11-134P22; RP11-636P15; RP11-78F17; CTD-2221P22; CTD-2011M14; RP11-626B11; and RP11-27K24. A marker may be a chromosomal region encoding a gene or not encoding a gene. A marker may be a molecule derived from a gene such as e.g. RNA like mRNA, siRNA, or a protein.

The hydrogen atom in position 5 of uracil is in 5-FU replaced by fluorine, and this leads to at least three different mechanisms of action as depicted in FIG. 1. By resembling UTP, 5-FU is incorporated in RNA by the RNA polymerases, and 5-FU inhibits the synthesis of DNA through inhibition of thymidylate synthase (TYMS or TS). Incorporation of 5-FU in DNA and alteration of membrane function have also been proposed as possible cytotoxic mechanisms.

TYMS inhibition has been suggested as the main cytotoxic result of prolonged exposure to low doses of 5-FU, whereas an RNA mediated effect may be the primary result of bolus administration [C Aschele 1992; AF Sobrero 1997]. The prognostic and predictive value of TYMS has been studied extensively, and it seems that high TYMS levels pre-dict resistance to TYMS inhibitors in advanced colorectal cancer [CG Leichman 1997, HJ Lenz 1998; A Paradiso 2000]. Genetic markers of TYMS seem to be predictive for 5-FU [T Watanabe 2001; H Elsaleh ASCO 2001, 493] while the results of IHC is less clear [T Takenoue 2000; D Edler 2002; CJ Allegra ASCO 2001, 491].

Dihydropyrimidine Dehydrogenase (DPD or DPYD) is a pyrimidine catabolic enzyme and is the initial rate limiting step in the pathway of uracil and thymine catabolism. It catabolizes approximately 80% of 5-FU, to a non-toxic compound [http://genome.ucsc.edu/, R. B. Diasio Clinical Pharmacokinetics, 16:215-237, 1989]. Concerning 5-FU sensitivity several studies have shown an inverse correlation, where low DPD seems to predicts responsiveness. By immunostaining this has been shown in breast cancer [J. Horiguchi British Journal of Cancer, 86(2):222-225, 2002], while consistent RNA expression in colorectal cancer [D. Salonga Clinical Cancer Research, 6(4):1322-1327, 2002], transitional cell cancer [Y. Hirano Cancer Chemotherapy and Pharmacology, 51(1):29-35, 2003], and gastrointestinal cell lines [Y. Kirihara International Journal of Oncology, 14(3):551-556, 1999] proved the same significance. In contrast Fujii and coworkers found no significant relationship of DPD activity in colorectal cancer [R. Fujii Int J Clin Oncol, 8:72-78, 2003], and similarly Jacob et al. found no correlation in mRNA expression of DPD and 5-FU response [C. Jakob Journal of Pathology, 204(5):562-568, 2004]. In a study on colorectal cancers higher RNA expression of DPD was found in normal tissue compared to cancer tissue [E. A. Kidd Clinical Cancer Research, 11(7):2612-2619, 2005]. The DPD gene is located on 1p21 and CGH-studies of breast cancer have showed a frequency of 50% of losses on 1p11-1p31 [P. O'Connell Breast Cancer Research and Treatment, 78(3):347-357, 2003]. Thus, DPD depletion occurs in several cancers that potentially may cause increased sensitivity towards 5-FU treatment.

Thymidine phosphorylase (TP) encoded by the ECGF1 gene catalyzes the reversible dephosphorylation of thymidine, deoxyguridine and their analogs. TP also has angiogenic properties and prevents tumor cells from entering apoptosis [H Ishitsuka 2000]. TP expression is elevated in many solid tumors including in situ and invasive breast carcinomas [Lee 1999; A Kanzaki 2002]. TP expression correlates with aggressive growth and invasion [Y Takebayashi 1996], and preclinical studies have shown a correlation between fluoropyrimidine resistance and high TP levels [B van Triest 2000].

Dihydrofolate reductase (DHFR) is important in cell proliferation, where it catalyzes the conversion of dihydrofolate (DHF) to tetrahydrofolate (THF). THF is required for purine biosynthesis as precursor of CH2-THF for the synthesis of thymine [G. J. Peters Biochimica Et Biophysica Acta-Molecular Basis of Disease, 1587(2-3):194-205, 2002, D. B. Longley Nature Reviews Cancer, 3(5):330-338, 2003]. Depletion of DHFR by antifolate inhibition interferes with thymidylate biosynthesis, and multiple studies have focused on the consequence of the DHFR depletion upon methotrexate exposure [E. Chu Journal of Biological Chemistry, 256(15):8470-8478, 1990]. Other studies have concerned translational auto regulation, mutations and amplifications as a mechanism of resistance against methotrexate in leukemia, reviewed in [D. Banerjee Biochimica Et Biophysica Acta-Molecular Basis of Disease, 1587(2-3):164-173, 2002]. A direct relation between 5-FU sensitivity and DHFR has not been intensively studied, but Backus and coworkers have shown that cancer cell lines grown in a low folate environment have higher sensitivity to 5-FU, whereby TYMS activity can be linked to folate level [H. H. J. Backus International Journal of Cancer, 87(6):771-778, 2000]. A study of RNA expression proved DHFR to be higher expressed in tumor tissue compared with normal tissue in colorectal cancer [E. A. Kidd Clinical Cancer Research, 11(7):2612-2619, 2005]. CGH-studies of breast cancer, reviewed in [P. O'Connell Breast Cancer Research and Treatment, 78(3):347-357, 2003], showed a frequency of losses of 45% on 5q, where DHFR is located, and as reduced folate is a co-substrate for TYMS, changes in DHFR could interfere with 5-FU sensitivity.

Thymidine kinase (TK1 alias TK) catalyses the phosphorylation of thymidine to deoxythymidine monophosphate. The gene is located at 17q25.2-q25.3. The gene contains many non-coding inserts and numerous Alu sequences. Nucleotide sequencing indicated considerable evolutionary conservation of the TK gene. Sequencing of the entire 12.9 kb human TK gene (Flemmington 1987) and flanking regions showed the TK gene is composed of 7 exons. In the 5-prime flanking region of the TK gene (Sauve 1990) a position of nucleotides sequences are located that can act as binding site for transacting factors as well as potential cis-acting sequences. The latter were compared with those of the promoter of the human PCNA gene. Both TK and PCNA are maximally expressed at the G1/S boundary of the cell cycle.

Intracellular folate homeostasis depends on 5,10-methylenetetrahydrofolate reductase (MTHFR), a critical enzyme in folate metabolism that catalyses the irreversible conversion of 5-methyltetrahydrofolate. The substrate 5,10-methylenetetrahydrofolate is required for DNA synthesis and for maintaining the balance of the nucleotide pool, whereas 5-methyltetrahydrofolate is required for methylation reactions, including the methylation of homocysteine to methionine and the maintenance of DNA methylation patterns (OMIM, 607093).

The cytoplasmic enzyme 5-methyltetrahydrofolate-homocysteine methyltransferase (methionine synthase, MTR) catalyses the transfer of a methyl group from methyltetrahydrofolate to homocysteine to generate tetrahydrofolate and methionine from homocysteine. The gene is located on chromosome 1q43.

A C677T polymorphism has been proposed to modulate the cytotoxic effect of 5-FU and MTX (Methotrexate) because the modes of action of 5-FU and MTX are critically depended on the cellular composition of folates. Sohn et al. (2004) showed that cell lines with mutant C677T MTHFR had decreased MTHFR activity, changed intracellular folate distribution, accelerated growth rate, and increased TYMS activity. In two cell lines from breast and colon cancer, respectively, the C677T mutation increased chemo sensitivity to 5-FU, but decreased the chemo sensitivity of the breast cell line to MTX. Based on these preliminary observations in vitro, we propose the CNC (copy number changes) of the MTHFR and TK genes are predictive for patient outcome when treated with 5-FU, MTX or combinatory regiments containing these drugs, e.g. CMF treatment.

In one embodiment the composition comprises at least two probes binding to at least two markers from the 5-FU pathway selected from the group consisting of Thymidylate synthase (TYMS), Dihydrofolate reductase (DHFR), Thymidine phosphorylase (TP), Dihydropyrimidine dehydrogenase (DPD), Methylenetetrahydrofolate reductase (MTHFR) and Thymidine kinase (TK) and 5-methyltetrahydrofolate-homocysteine methyltransferase (methionine synthase, MTR). In one embodiment of the composition according to the invention said at least two markers from the 5-FU pathway are TYMS and DHFR. In another embodiment the composition according to the invention comprises at least three probes binding to at least three markers from the 5-FU pathway. A non-limiting example of such three markers is e.g. TYMS, DHFR and TS.

In one embodiment the composition according to the invention comprises at least one DNA probe binding to at least one marker from the 5-FU pathway selected from the group consisting of TYMS, DHFR, TP, DPD, MTHFR, TK and MTR. In other embodiments, the composition comprises two, three, four, five, six or seven probes binding to markers from the 5-FU pathway, wherein at least one or more or all of the probes are DNA probes. The marker(s) may independently be TYMS, DHFR, TP, SPD, MTHFR and TK.

In a further embodiment, the composition comprises at least one probe binding to at least one reference marker.

In one embodiment the composition according to the invention comprises at least one probe binding to at least one marker from the 5-FU pathway selected from the group consisting of TYMS, DHFR, TP, DPD, MTHFR, TK and MTR, and at least one probe binding to a reference marker, wherein at least one of said probes is a DNA probe. In other embodiments, such composition comprises two, three, four, five, six or seven probes binding to markers from the 5-FU pathway. The marker(s) may independently be TYMS, DHFR, TP, SPD, MTHFR and TK.

A reference marker is a marker as described above that may be selected as a reference marker because it is not the marker of interest. A reference marker is sometimes included when a relative level of a marker is to be determined. For example, when the relative gene copy number in a sample is to be calculated, the ploidy of the cell must be identified, therefore a marker indicating the number of chromosomes carrying the reference marker gene may be used. The reference markers used may be a reference marker gene such as a centromer or another gene or chromosomal region, or it may a reference marker protein such as a centrosome or another protein. A reference marker may also be a reference marker RNA or any other reference marker that may serve as a reference.

In one embodiment of the invention said at least one reference marker of the composition may be selected from any marker not comprised in the 5-FU pathway. In another embodiment of the invention said at least one reference marker of the composition is a nucleic acid sequence from a non-coding region of a chromosome. In one embodiment, the probe binding to the reference marker is a DNA or PNA probe, or a combination of a DNA probe and a PNA probe.

In one embodiment of the invention said at least one reference marker of the composition is a centromere (Cen). It may also for example be a gene product, such as a centrosome protein.

In one embodiment of the invention said at least one reference marker of the composition is selected from the group consisting of Cen1, Cen2, Cen5, Cen10, Cen12, Cen17, Cen18, and Cen22.

A large component of the human genome comprises repeat sequences that may cause background staining. The most common repeats are the short and long interspersed nuclear elements (SINE and LINE respectively) where the most abundant repeats in the former are Alu repeats [70]. The background can be suppressed or blocked by addition of unlabelled probes binding to the randomly distributed repeat sequence. One approach is the development of nucleic acid molecules or nucleic acid analogue molecules like PNA directed against specific randomly distributed repeat sequence. Another approach is the use of a pool of unlabelled human DNA for blocking such as e.g. Cot1 DNA or total human DNA. Both approaches may be combined to obtain optimal background suppression. It may be advantageous to use a combination of DNA and PNA blocking probes.

In one embodiment the composition further comprises at least one blocking probe capable of blocking, suppressing or preventing the interaction of a marker with other probes. Such markers to be blocked may be one or more segments of randomly distributed repeat sequence selected from the group consisting of: SINEs and LINEs. Non-limiting examples of the SINEs and LINEs may be selected from the group consisting of: Alu-repeats, Kpn-repeats, di-nucleotide repeats, tri-nucleotide repeats, tetra-nucleotide repeats, penta-nucleotide repeats and hexa-nucleotide repeats. Non-limiting examples of the one or more segments of randomly distributed repeat sequences may be a fraction, or part, of a unit repeat of either: i) an Alu-repeat sequence; or ii) a consensus sequence of an Alu-repeat sequence. In one embodiment, such blocking probe is composed on DNA probes or fragments, PNA probes, or a combination of DNA probes and/or DNA fragments and/or PNA probes.

In one embodiment the present invention relates to a method for determining the level of at least two markers from the 5-FU pathway in an isolated sample from a subject by an analysis comprising the steps of, detecting a signal from each of at least two markers from the 5-FU pathway in said isolated sample, and determining the level based on the at least two signals detected. In particular, the level of three, four, five or six markers may be determined. The markers may be selected independently from TYMS, DHFR, TP, DPD, MTHFR, TK and MTR. In a special embodiment, the level is indicative of amplifications or deletions or a combination of amplification(s) and deletion(s). In certain cases, the level is indicative of amplification(s) and/or deletion(s) in combination with a normal level. In another embodiment of the method according to the invention said method further comprises steps of detecting a signal from at least one reference marker, and determining the level based on correlation of a signal from each of at least two markers from the 5-FU pathway and a signal from at least one reference marker.

In one embodiment, the present invention relates to a method for determining the level of at least one marker from the 5-FU pathway in an isolated sample from a subject by an analysis comprising the steps of, detecting a signal from the at least one marker from the 5-FU pathway in said isolated sample using at least one DNA probe binding to at least one marker from the 5-FU pathway, and determining the level based on the at least one signal detected. In particular, the level of two, three, four, five or six markers may be determined. The marker(s) may be selected independently from TYMS, DHFR, TP, DPD, MTHFR, TK and MTR. In a special embodiment, the level is indicative of amplification(s) or deletion(s) or a combination of amplification(s) and deletion(s). In certain cases, the level is indicative of amplification(s) and/or deletion(s) in combination with a normal level. In another embodiment of the method according to the invention said method further comprises steps of detecting a signal from at least one reference marker, and determining the level based on correlation of a signal from each of at least two markers from the 5-FU pathway and a signal from at least one reference marker.

In one embodiment, the present invention relates to a method for determining the level of at least one marker from the 5-FU pathway in an isolated sample from a subject by an analysis, comprising the step of detecting a signal from at least one marker from the 5-FU pathway in said isolated sample using at least one probe binding to the at least one marker from the 5-FU pathway, detecting a signal from at least one reference marker in said isolated sample using at least one probe binding to the at least one reference marker, wherein one of said probes is a DNA probe, and determining the level of said at least one marker from the 5-FU pathway based on correlation of a signal from said at least one marker from the 5-FU pathway and a signal from said at least one reference marker. In particular, the level of two, three, four, five or six markers may be determined. The marker(s) may be selected independently from TYMS, DHFR, TP, DPD, MTHFR, TK and MTR. In a special embodiment, the level is indicative of amplification(s) or deletion(s) or a combination of amplification(s) and deletion(s). In certain cases, the level is indicative of amplification(s) and/or deletion(s) in combination with a normal level.

The subject may be any individual or human being. The subject may be a healthy subject or the subject may be a non-healthy subject, such as a subject having cancer or suspected of having cancer. Examples of cancers are e.g. breast cancer, lung cancer, colorectal cancer, prostate cancer, lung cancer, head & neck cancer, stomach cancer, pancreas cancer, esophagus cancer, liver cancer, and bladder cancer.

A number of analyses exist, many of which are known in the art. The precise analysis used in the method according to the invention should be carefully selected according to the nature of the markers and the probes. Fluorescence in-situ hybridization (FISH) has become an important tool for determining the number, size and/or location of specific DNA sequences in cells. Typically, the hybridization reaction fluorescently stains the sequences so that their location, size and/or number can be determined using fluorescence microscopy, flow cytometry or other suitable instrumentation. DNA sequences ranging from whole genomes down to several kilobases can be studied using current hybridization techniques in combination with commercially available instrumentation. In Comparative Genomic Hybridization (CGH) whole genomes are stained and compared to normal reference genomes for the detection of regions with aberrant copy number. In the m-FISH technique (multi color FISH) each separate normal chromosome is stained by a separate color (Eils et al, Cytogenetics Cell Genet 82: 160-71 (1998)). When used on abnormal material, the probes will stain the aberrant chromosomes thereby deducing the normal chromosomes from which they are derived (Macville M et al., Histochem Cell Biol. 108: 299-305 (1997)). FISH-based staining is sufficiently distinct such that the hybridization signals can be seen both in metaphase spreads and in interphase nuclei. Single and multicolor FISH, using nucleic acid probes, have been applied to different clinical applications generally known as molecular cytogenetics, including prenatal diagnosis, leukemia diagnosis, and tumor cytogenetics. Other methods may be RT-PCR and ISH including CISH. In particular, a combination of FISH and CISH may be used, e.g. by labeling the probe with a fluorescent label or chromogen label, and subsequently converting the FISH signal into a CISH signal or visa versa. Alternatively, a probe can be labeled with both a fluorescent and a chromogen label so as to enable separate detection of the FISH signal or the CISH signal.

Protein based assays may for example be Immuno based techniques such as e.g. Immunohistochemistry (IHC), Immunocytochemistry (ICC), Flow cytometry, ELISA, Blotting, Precipitation.

Genes, mRNAs and proteins may all be relevant predictive markers for an individual stratified treatment. For simplicity only genes are mentioned below, but similar arrays can be made for either mRNA or protein detection. The simplest way may be to cut the relevant number of sections from paraffin embedded tissue and hybridize a probe to each section. Alternatively frozen tissue can be used or imprints. This approach may be used for initial testing. Here each target gene and the corresponding reference gene are analyzed on separate sections requiring only two different colors. However, multiplex assays, wherein all genes are tested in a single hybridization on the same section, are also contemplated. Several other possibilities exist, mostly based on cover-slip probes. Hybridization demands only standard conditions. For most probes an internal reference, such as e.g. a centromeric probe, should be included. The gene probe and the reference probe should be labeled in different colors such as e.g. red and green, respectively. The blue DAPI color may be used for counterstaining to assist tissue localization and identification. Availability of control Hematoxylin-Eosin cut section may also useful.

Studies of higher-order chromatin arrangements are an essential part of ongoing attempts to explore changes in epigenomic structure and their functional Implications during development and cell differentiation. Between cell divisions the chromatin fiber of each chromosome is restricted to a subvolume of the interphase cell nucleus called chromosome territory (CT). The internal organization of these territories shows a cell type specific constitution [Stadler 2004]. The repositioning of chromosomal loci during differentiation may be a consequence of general changes in CT morphology, not necessarily related to transcriptional changes. The nuclear topological arrangement of CTs has been conserved during primate evolution over a period of about 30 million years. Recent evidence shows that the positioning of chromatin in human lymphocyte nuclei is correlated with gene density [Tanabe 2002]. Gene density-related differences in the radial arrangement of CTs have been reported [Croft 1999] with gene-poor, late replicating CTs located toward the nuclear periphery and gene-dense, early replicating CTs in the nuclear periphery. In tumor cell nuclei a partial loss of radial chromatin order has been observed [Cremer 2003]. Using new tools for studying the three-dimensional (3D) chromosome arrangements [Bolzer 2005] it has been shown that chromatin domains, which are gene-poor, form a layer beneath the nuclear envelope, while gene-dense chromatin is enriched in the nuclear interior.

The level of a marker may be measured as the actual amount of a marker present in the sample. For genes it may for example be the gene copy number and for proteins it may be the number of proteins. The level may also be reported as a ratio, where the amount of marker of interest is correlated to the amount of a reference marker. The level of a marker may in some cases be correlated to a condition or a disease, and may therefore be used for describing and/or predicting such conditions or diseases. Identification of such levels is often found empirically and may be dependent on the actual condition or disease, and the analysis used. Sometimes such levels are referred to as cut-off values.

In a normal cell two copies of each of our genes are present. Theoretically, two signals should be visible. However, due to cutting of sections from paraffin embedded tissue, whole nuclei will not be present. Therefore, a difference between theoretical and actual number of signals is observed and cut-off levels between normal and abnormal number of signals pr. cell will have to be determined empirically. Using a reference probe, two reference probe signals should be seen in a normal cell, and theoretically the ratio between signals from gene probe and reference probe should be 1 (one). However, due to technical, biological and statistical reasons this absolute value is determined as a range e.g. between 0.8 and 2.0 in the case of HER2 FISH (package insert, Dako HER2 FISH pharmDx™ kit, code K5331). The FISH assay can be performed with and without one or more reference probes (HER2 FISH products using both modalities are on the market). Without a reference probe only signals in one color from the target gene probe are scored, and the cut-off between normal and amplified is 4-5, although the theoretical value is 2. Deletions cannot be scored in an assay without a reference probe or a reference sample.

A FISH assay may include one or more reference probes in addition to the marker gene probe, labeled in different colors. For example the gene copy number may be calculated by using a reference probe. Signal from each marker gene copy and signal from the corresponding reference gene copy are detected and the ratio is calculated. The reference is a measure of the ploidy level, thus the number of chromosome copies, of the nucleus. The most accepted cut-off value of a normal gene copy number is indicated by a ratio between 0.8 and 2.0. Gene deletion is indicated by a ratio below 0.8, whereas gene amplification is indicated by a ratio above 2.0. However, other cut-off values have been reported and used [Järvinen, 1999], e.g. between 0.67 and 1.5. A true cut-off value should be determined based on patient outcome data [Bonetti and Gelber, 2000;], and this has not yet been done. For most markers it is expected that a normal gene copy number will be predictive for response to 5-FU, whereas a decreased gene copy number will be predictive for a reduced or a lack of response to treatment with 5-FU chemotherapy. However, for some markers an inverse correlation may exist. For example deletion of the DPD gene is expected to indicate responsiveness and it has been speculated if amplification would indicate non-responsiveness. However, the impact of amplifications has not yet been fully understood. The study of the predictive value of TOP2A gene copy number (GCN) changes showed that deletions and amplifications both predicted response to anthracycline treatment while patients the normal GCN did not benefit from the treatment [Knoop 2003].

The probe binding to a reference marker may be targeted against the centromeric region of the chromosome where the target of interest is located. By applying the reference on the same chromosome the specific ploidy level of the given chromosome is decisive of whether the genomic probe will be found amplified, deleted or normal. Both nucleic acid probes, nucleic acid analogue probes as well as protein probes may be employed. In spite of the great homology in the centromeric DNA of humans, clones have been identified and constructed, containing human chromosome specific centromeres for use in FISH. Probe length may be dramatically reduced without reduction of the signal intensity when probes targeted against centromeric repeat sequences are used, The advantage of using centromeric reference probes is that they do not contribute to background staining as they do not contain SINEs and LINEs.

Centromeres at chromosome 1, 2, 5, 10, 12 17, 18 and 22 have been found to be specifically identified by FISH probes derived from clone sequences that can be used directly as reference probes. However, synthetic peptide nucleic acid (PNA) probes may be chosen for centromere detection in FISH, because of their DNA specificity and higher signal intensity, with a reduction of unspecific background. A PNA is a synthetic oligonucleotide where the backbone mimics a peptide instead of the deoxyribose phosphodiester backbone of DNA. For PNA construction a sequence of about 10-25 bases is useful. Alternatively a locus specific probe (LSP) may be used as reference. This should preferably be placed on the opposite chromosome arm than the gene of interest, to eliminate incorrect probe to reference ratio if whole arm deletions occurs. The reference probe should not be placed in a region that has any relation to genome aberrations in cancer.

One embodiment of the invention relates to a method for predicting the outcome of 5-FU treatment in a subject, comprising the steps of determining the level of at least two markers from the 5-FU pathway in an isolated sample from a subject by an analysis, and predicting the outcome of the 5-FU treatment in said subject based on the level determined.

One embodiment of the invention relates to a method for predicting the outcome of 5-FU treatment in a subject further comprising detecting a signal from at least one reference marker, and determining the level of at least two markers from the 5-FU pathway based on correlation of a signal from each of at least two markers from the 5-FU pathway and a signal from at least one reference marker.

Another embodiment of the invention relates to a method for predicting the outcome of treating a subject with 5-FU, comprising the steps determining the level of gene aberration of at least two markers from the 5-FU pathway in an isolated sample from a subject by an analysis, and predicting the outcome of the 5-FU treatment in said subject based on the level determined.

One embodiment of the invention relates to a method for predicting the outcome of 5-FU treatment in a subject further comprising detecting a signal from at least one reference marker, and determining the level of gene aberration of at least two markers from the 5-FU pathway based on correlation of a signal from each of at least two markers from the 5-FU pathway and a signal from at least one reference marker.

One embodiment of the invention relates to a method for predicting the outcome of 5-FU treatment in a subject, comprising the steps of determining the level of at least one marker from the 5-FU pathway in an isolated sample from a subject by an analysis using a DNA probe binding to a marker from the 5-FU pathway, and predicting the outcome of the 5-FU treatment in said subject based on the level determined.

In another embodiment, the method further comprises detecting a signal from at least one reference marker, and determining the level of the at least one marker from the 5-FU pathway based on correlation of a signal from the at least one marker from the 5-FU pathway and a signal from the at least one reference marker.

Another embodiment of the invention relates to a method for predicting the outcome of treating a subject with 5-FU, comprising the steps determining the level of gene aberration of at least one marker from the 5-FU pathway in an isolated sample from a subject by an analysis using at least one DNA probe binding to a marker from the 5-FU pathway, and predicting the outcome of the 5-FU treatment in said subject based on the level determined. In one embodiment, such method further comprises detecting a signal from at least one reference marker, and determining the level of gene aberration of the at least one marker from the 5-FU pathway based on correlation of a signal from the at least one marker from the 5-FU pathway and a signal from at least one reference marker.

One embodiment of the invention relates to a method for predicting the outcome of 5-FU treatment in a subject, comprising the steps of determining the level of at least one marker from the 5-FU pathway in an isolated sample from a subject by an analysis using at least one probe binding to said at least one marker from the 5-FU pathway, detecting a signal from at least one reference marker using a probe binding to at least one reference marker, wherein one of said probes is a DNA probe, and predicting the outcome of the 5-FU treatment in said subject based on the level determined, said level being based on correlation of a signal from said at least one marker from the 5-FU pathing based on correlation of a signal from said at least one marker from the 5-FU pathway and a signal from said at least one reference marker.

Another embodiment of the invention relates to a method for predicting the outcome of treating a subject with 5-FU, comprising the steps determining the level of gene aberration of at least one marker from the 5-FU pathway in an isolated sample from a subject by an analysis using at least one probe binding to said at least one marker from the 5-FU pathway, detecting a signal from at least one reference marker using a probe binding to at least one reference marker, wherein one of said probes is a DNA probe, and predicting the outcome of the 5-FU treatment in said subject based on the level determined, said level of gene aberration being based on correlation of a signal from said at least one marker from the 5-FU pathway and a signal from said at least one reference marker.

Identification of gene aberration may be performed by using specific probes, one binding to a normal gene copy and another binding to an aberrant gene copy. By labeling the two probes differently it would be possible to identify the presence and the copy number of an aberrant gene. Sometimes only one copy of a gene is aberrant and sometimes two or more copies are aberrant.

Gene aberration covers any changes in the DNA and may be e.g. deletion, amplification, translocation, mutation, insertion, fusion, inversion and DNA methylation In one embodiment of the invention the method further comprises contacting the sample with a composition of the invention.

In one embodiment of the invention the analysis is a gene analysis.

In one embodiment of the invention the sample is derived from a tissue selected from the group consisting of breast, lung, colorectal, prostate, lung, head & neck, stomach, pancreas, esophagus, liver, and bladder.

In one embodiment of the invention the sample is a tissue sample, a cell preparation, a cell fragment preparation an isolated or enriched cell component preparation and a protein preparation.

The sample may be isolated and processed using standard protocols. The sample isolated from a subject may be a sample originating from various tissues such as e.g. breast, lung, colorectal, prostate, lung, head & neck, stomach, pancreas, esophagus, liver, and bladder or other relevant tissues and neoplasia thereof. The sample may take any form such as e.g. a tissue sample, a cell preparation, a cell fragment preparation, an isolated or enriched cell component preparation or a protein preparation. Non-limiting examples may be: Tissue may be a biopsy, cut section. Cell preparation may be any cell suspension, blood sample, fine needle aspiration, ascites fluid, sputum, peritoneum wash, lung wash, urine, faeces, cell scrape, cell smear, cytospin or cytoprep cells. Cell fragment preparations may e.g. be obtained by cell homogenizing, freeze-thaw treatment or cell lysing. The isolated sample may be treated in many different ways depending of the purpose of obtaining the sample and depending on the routine at the site. Often the sample is treated with various reagents to preserve the tissue for later sample analysis, alternatively the sample may be analyzed directly. Examples of widely used methods for preserving samples are formalin-fixed followed by paraffin-embedding and cryo-preservation.

In one embodiment of the invention the subject will be, is or has been receiving at least one anti cancer treatment.

Cytotoxic chemotherapy with DNA synthesis inhibitors (as 5-FU) has demonstrated activity in a large range of malignancies and both in early and late stages of the disease. Activity has been observed both when 5-FU or analogs are given as single agents and in combinations with other cytotoxic agents or other treatment modalities and with a wide range of administrations including bolus and continuous infusion and oral administration. Activity has even been observed following re-treatment after using another DNA synthesis inhibitor or a different schedule or with the same regimen in different stages of the disease. Prior to the test and treatment with 5-FU or analogs the subject may have received one of more regimens of cytotoxic chemotherapy as well as other treatment modalities including endocrine therapy, radio-therapy and targeted therapy. The treatment may be neoadjuvant (before surgery) or adjuvant (precise after surgery) or treatment for metastatic disease. The cytotoxic chemotherapy received may include 5-FU, especially when re-treatment is intended after demonstration of prior activity or a disease-free interval following adjuvant treatment.

In one embodiment of the invention the at least one treatment is a monotherapy or a combinatorial therapy.

In one embodiment of the invention the combinatorial therapy is given sequentially or simultaneously.

In one embodiment of the invention the treatment is selected from the group consisting of a surgical treatment, radio-therapeutical treatment and chemo-therapeutical treatment.

In one embodiment of the invention the chemo-therapeutical treatment is selected from the group consisting of cytotoxic, anti-hormone and targeted therapy.

In one embodiment of the invention the chemo-therapeutical treatment is a cytotoxic chemotherapeutical treatment.

It is anticipated that a level below the normal gene copy number of at least one of the markers from the 5-FU pathway is predictive for less susceptibility to 5-FU treatment.

In one embodiment of the invention the probe(s) used in the method according to the invention may be nucleic acid probes or nucleic acid analogue probes as disclosed.

In one embodiment of the invention the probes comprised in the method are binding to at least two markers selected from the 5-FU pathway under stringent conditions. In another embodiment, the DNA probe comprised in the method is binding to at least one marker selected from the 5-FU pathway under stringent conditions.

Probes may bind to the marker of interest and hybridize under stringent conditions. Those of ordinary skill in the art of hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/marker sequence combination is often found by the well-known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Optimal stringency for an assay may be experimentally determined by examination of each stringency factor until the desired degree of discrimination is achieved. Generally, the more closely related the background causing nucleic acid contaminates are to the target sequence, the more carefully stringency must be controlled. Suitable hybridization conditions will thus comprise conditions under which the desired degree of discrimination is achieved such that an assay generates an accurate (within the tolerance desired for the assay) and reproducible result. Nevertheless, aided by no more than routine experimentation and the disclosure provided herein, those of skill in the art will easily be able to determine suitable hybridization conditions for performing assays utilizing the methods and compositions described herein.

Non-limiting examples of stringent conditions are described in the experimental procedure below and further non-limiting examples may be found in chapter 11 in Peptide Nucleic Acids, Protocols and Applications, Second Ed. Editor Peter E Nielsen, Horizon Scientific Press, 2003.

The markers or marker from the 5-FU pathway are/is independently selected from the group consisting of TYMS, DHFR, TP, DPD, MTHFR, TK and MTR.

Suitably, TYMS, DHFR, TP, DPD, MTHFR, TK or MTR may be detected alone. Examples of suitable combinations are TYMS and DHFR; TYMS, DHFR and TP; and TYMS, DHFR and TK. When the markers are determined in combination, it is to be understood that the detection is done using separate samples or the same sample.

In one embodiment of the invention the subject is having or suspected of having cancer.

In one embodiment of the invention the cancer is selected from the group consisting of breast cancer, lung cancer, colorectal cancer, prostate cancer, lung cancer, head & neck cancer, stomach cancer, pancreas cancer, esophagus cancer, liver cancer, and bladder cancer.

In one embodiment of the invention the method is further contemplating the use of image analysis systems.

Manual reading of the result of many samples is very time consuming. Therefore, it would be a great help to have access to automated systems. The reading of for example many fields of hybridization would be aided by fluorescence image analysis with high speed scanning facilities. MetaSystems is an example of a provider of an image analysis system that might be used.

The present invention further relates to the use of the composition as disclosed above for determining the level of at least one marker (using at least one DNA probe) or at least two markers (using at least two probes) selected from the 5-FU pathway in an isolated sample from a subject. The present invention further relates to the use of the composition as disclosed above for determining the level of at least one marker selected from the 5-FU pathway and at least one reference marker in an isolated sample from a subject, wherein at least one of such probes is a DNA probe.

In one embodiment of the invention the composition as defined above is used for determining the level of gene aberration. In one embodiment of the invention the composition is used for predicting the outcome of a 5-FU treatment in a subject. In one embodiment of the invention the composition is used, wherein the subject is a subject having or suspected of having cancer. In one embodiment of the invention the composition is used, wherein the cancer selected from the group consisting of breast cancer, lung cancer, colorectal cancer, prostate cancer, lung cancer, head & neck cancer, stomach cancer, pancreas cancer, esophagus cancer, liver cancer, and bladder cancer.

The present invention furthermore relates to a kit for determining the level of at least two markers from the 5-FU pathway in an isolated sample from a subject by an analysis, the kit comprising a composition comprising at least two probes binding to at least two markers from the 5-FU pathway, and instructions for using the composition. In one embodiment the kit for determining the level of at least two markers from the 5-FU pathway in an isolated sample from a subject by an analysis, further comprises a probe binding to a reference marker.

One embodiment of the invention relates to a kit for predicting the outcome of a 5-FU treatment in an isolated sample from a subject by an analysis, the kit comprising a composition comprising at least two probes binding to at least two markers from the 5-FU pathway, and instructions for using the composition. In one embodiment the kit for predicting the outcome of a 5-FU treatment in an isolated sample from a subject by an analysis further comprises at least one probe binding to a reference marker.

The present invention furthermore relates to a kit for determining the level of at least one marker from the 5-FU pathway in an isolated sample from a subject by an analysis, the kit comprising a composition comprising at least one DNA probe binding to at least one marker from the 5-FU pathway, and instructions for using the composition. In a further embodiment, such kit further comprises at least one probe binding to a reference marker.

One embodiment of the invention relates to a kit for predicting the outcome of a 5-FU treatment in an isolated sample from a subject by an analysis, the kit comprising a composition comprising at least one DNA probe binding to at least one marker from the 5-FU pathway, and instructions for using the composition. In one embodiment the kit for predicting the outcome of a 5-FU treatment further comprises a probe binding to a reference marker.

The present invention furthermore relates to a kit for determining the level of at least one marker from the 5-FU pathway in an isolated sample from a subject by an analysis, the kit comprising a composition comprising at least one probe binding to at least one marker from the 5-FU pathway, and at least one probe binding to at least one reference marker, wherein at least one of said probes is a DNA probe, and instructions for using the composition.

One embodiment of the invention relates to a kit for predicting the outcome of a 5-FU treatment in an isolated sample from a subject by an analysis, the kit comprising a composition comprising at least one probe binding to at least one marker from the 5-FU pathway, and at least one probe binding to at least one reference marker, wherein at least one of said probes is a DNA probe, and instructions for using the composition.

The kit according to the invention may be constructed in any suitable way. Non-limiting embodiments therefore are as follows.

In one embodiment the kit comprises four probes for markers from the 5-FU pathway and four probes for reference markers which may be visualized using individual colors (one 8-color stain) or may be visualized using at least two colors (four separate 2-color stains).

In one embodiment the kit comprises three probes for markers from the 5-FU pathway and three probes for reference markers which may be visualized using individual colors (one 6-color stain) or may be visualized using at least two colors (three separate 2-color stains).

In one embodiment the kit comprises two probes for markers from the 5-FU pathway and two probes for reference markers which may be visualized using individual colors (one 4-color stain) or may be visualized using at least two colors (two separate 2-color stains).

In one embodiment, the kit comprises one DNA probe for a marker from the 5-FU pathway and one probe for a reference marker which may be visualized using individual colors (2-color stain).

In one embodiment the kit comprises four probes for markers from the 5-FU pathway and two probes for reference markers which may be visualized using individual colors (one 6-color stain) or may be visualized using at least two colors (two separate 3-color stains).

In some embodiments the kit comprises three probes for markers from the 5-FU pathway and two probes for reference markers which may be visualized using individual colors (one 5-color stain) or may be visualized using at least two colors (two or three separate stains).

In one embodiment the kit comprises two probes for markers from the 5-FU pathway and two probes for reference markers which may be visualized using individual colors (one 4-color stain) or may be visualized using at least two colors (two separate 2-color stains).

In one embodiment the kit comprises four probes for markers from the 5-FU pathway and one probe for reference markers which may be visualized using individual colors (one 5-color stain) or may be visualized using at least two colors (two or three separate stains).

In one embodiment the kit comprises three probes for markers from the 5-FU pathway and one probes for reference markers which may be visualized using individual colors (one 4-color stain) or may be visualized using at least two colors (two separate 2-color stains).

In one embodiment the kit comprises two probes for markers from the 5-FU pathway and one probe for reference markers which may be visualized using individual colors (one 3-color stain).

In one embodiment the kit comprises 1 probe for markers from the 5-FU pathway and one probe for reference markers which may be visualized using individual colors (one 2-color stain).

EXAMPLES

This invention is now illustrated by the following examples that are not intended to be limiting in any way.

Example 1

Genomic FISH Probes for 5-FU Assay and Experimental Procedures

FIG. 1.b shows the 4 main markers for which assays containing gene probes and references have been constructed.
List of Marker Genes:
1. TYMS (Thymidylate synthase) on 18p11.32
2. TP (ECGF1) (Thymidine phosphorylase) on 22q13.32
3. DPD (DPYD) (Dihydropyrimidine dehydrogenase) on 1p22
4. DHFR (Dihydrofolate reductase) on 5q11.2-q13.2
Reference is made to FIGS. 3-8.

A proper signal intensity of a FISH probe is dependent on the length of the probe and the type and amount of fluorochromes present. We found that approximately 4000 texas red (TxR)-molecules may be used for detection, which is normally obtained by a probe of 200-400 kb. The green FITC probe requires about 10,000 molecules. This requires a probe larger than 500 kb which is extensively labeled.

Clones covering the target gene sequence of were identified on the UCSC Genome Browser. By genomic alignments of BAC ends, the clones were localized in the human genome, and when choosing clones, length and identity match was taken into consideration. In some cases combinations of more clones is necessary to obtain a probe with high signal intensity, therefore some clones were selected as extension of each other. FIG. 3 shows the clones selected to cover the sequence of the four genes, while FIG. 4 shows the selected reference probes. All clones were tested by comparison of the restriction pattern between a theoretical digest and the actual DNA, where the total sequence was identified from full length clones and combined with the relevant vector. The digest was performed with BamHI.

Cell Line Culturing and Harvesting

The cell line BT-20 was chosen as a validation tool for verification of TYMS amplification detection. This cell line have whole arm gains of 5p, 7p, 10p, 16q, 18q and 20q and a regional copy number increase at 4q32-q34 and 6q21-q22 [55]. No deviations from the method described in the previous chapter were made during culturing and replating. Two different slide preparations were performed when harvesting to optimize the metaphase spread formation. First the slides were washed in cold milliQ water before use, and secondly slides were polished shortly with 70% EtOH before washing in cold milliQ water. The number of metaphases was evaluated in the microscope, and it seemed that more was present after the ethanol pre-treatment. Not many metaphases appeared per slide, and perhaps optimization of the hypoton solution could improve the yield, but for this study sufficient spreads were obtained.

Preparation of Cells for Cyto-Slides

The cell line BT-20 were cultured in Eagles Minimum Essential Medium with Earles salt (Gibco) supplemented with 10% fetal bovine serum (In vitro A/S), 0.1mM nonessential amino acids (Gibco), 1 mM sodium pyruvate (Gibco), 2 mM L-glutamine (Gibco) and penicillin/streptomycin (Gibco) and incubated in a Sanyo MCO-20 AIC CO2 incubator at 37° C. and 5% CO2. Media was changed 2-3 times a week, and when reaching confluence, the cells were detached by mild treatment with 0.25% trypsin with EDTA (Gibco) for 8-12 min at 37° C., after a short rinse with PBS (D-PBS, Gibco). Cells obtained from human blood, were washed twice with PBS before culturing in RPMI 1640 supplemented with 10% fetal bovine serum (In vitro A/S), 0.1 mM nonessential amino acids (Gibco), 1 mM sodium pyruvate (Gibco), 2 mM L-glutamine (Gibco) and penicillin/streptomycin (Gibco) and incubated in a Sanyo MCO-20 AIC CO2 incubator at 37° C. and 5% CO2. For metaphase spreads 10 µL Kariomax Colcemid (Gibco/BRL) was added per 10 mL cell culture, and incubated at 37° C. for 2 h to inhibit spindle formation, thereby stopping cells in metaphase. After trypsination the cells were resuspended in 5 mL 60 mM hypoton-solution (60 mM KaCl) for 20 min followed fixation in fiesh-made fixative (3:1 volume of methanol:Acetic acid) and left for 5 min. Cells were isolated by centrifugation at 10 min at 189×G and was resuspended in 10 mL of fixative. This step was repeated two times before applying fixative in a volume producing a slightly cloudy suspension. Superfrost slides from Menzel-Glaserr were polished shortly with 70% EtOH before washing in cold milliQ water. Excess water was removed and 10 µL of cell suspension was applied in two spots on each slide, and dried for 5 min in 50-60% humidity, followed by drying in a fume hood for 1-2 days. The slides were pretreated for 2 min in 3.7% formaldehyde in TBS (50 mM Tris pH 7.6 and 0.15M NaCl), washed in PBS (10 mM NaPO4 and 0.145M NaCl, pH7.2), and dehydrated in a series of cold 70%, 85%, and 96% ethanol for 2 min each and air-dried priory to addition of probes.

Preparation of Tissue for Histo-Slides

Formalin-fixed paraffin embedded tissue were cut to sections of 3-7 µm. Paraffin was removed by placing slides 2×5 min in xylene, washing in a series of 99%, 96%, and 70% ethanol, for 2 min at each, before washing for 2 min in Wash Buffer (Vial 3, Histology FISH Accessory Kit K599, Dako). Slides were incubated 10 min in Pre-Treatment solution (Vial 1, Histology FISH Accessory Kit K599, Dako), preheated to 97° C. using microwave (MicroMED, T/T Mega, Milestone). Slides were allowed to cool down in 15 min in Pre-Treatment solution before washing 2×3 min in Wash Buffer. Surplus water was removed and 5-8 drops of cold (2° C.-8° C.) Ready-to-use Pepsin (Vial 2, Histology FISH Accessory Kit K599, Dako) was added each slide. Slides were incubated 10 min at room temperature. Pepsin was hereafter removed by washing slides 2×3 min in Wash buffer. Finally slides were washed in a series of 70%, 96%, and 99% ethanol, 2 min at each concentration, and air-dried priory to addition of probes.

Preparation of DNA for FISH

Isolation of unique sequence probe: The initial step in the preferred method of making probes is to amplify the clone by growth, before isolation, and purification of the DNA having the unique sequence insert from the growth host (Zhao E, Stodolsky M. Methods in Molecular Biology. Library Construction, Physical Mapping, and Sequencing. Vol I, first ed. 2004. Humana Press).

The probe precursor DNA was directly labeled with fluorochrome by nick-translation. To label the probe precursor DNA, on ice, 10 µg of DNA was resuspended in 0.250 mL reaction buffer consisting of 25 µL 10× Nick translations buffer (Tris-HCl 500 mmol/L, 100 mmol/L MgCl2, 1 mmol/L DTT, 100 mg/L BSA, pH 7.5), 25 µL 10×dNTP-mix (Tris-HCl 50 mmol/L, 10 mmol/L EDTA, 0.5 mmol/L dATP, 0.5 mmol/L dGTP, 0.5 mmol/L dCTP, 0.34 mmol/L dTTP, pH 7.6), 4 µL of dUTP-fluorochrome (1 mmol/L), 10 µL DNA polymerase I (Invitrogen, 10 U/µL), and 0.3 µL DNase I (Sigma-Aldrich, empirically determined). Mixture was incubated at 15° C., for 4 hours, before stopping the reaction by adding 25 µL 500 mmol/L EDTA, and incubating at 65° C. for 10 minutes. Unincorporated nucleotides were removed by centrifugation using Microcon YM-10 Centrifugal Filter Devices (Millipore). The purified labeled probe was resuspended in 25 µL TE-solution (Tris-HCl 10 mmol/L, 0.1 mmol/L EDTA, pH 8.0). This solution was stored at −20° C. until use.

Fish Protocol

The hybridization mix for one target area on a slide contained between 2-150 ng of target and reference probe, 1 µg sonicated unlabelled total human DNA dissolved in hybridization buffer (45% formamid, 10% dextransulphate, 0.3M NaCl, 5 mM sodium phosphate, 5 µmol/L PNA blocking Oligo). On each target area, 10 µL hybridization mix was applied, sealed with a cover slip and rubber cement, followed by denaturisation at 82° C. for 5 min, and hybridization at 45° C. for 18 h using a hybridizer (Dako). After hybridization the cover slip was removed and the slide was washed for 10 min in Stringent Wash buffer (0.2×SSC, 0.1% Triton X-100) preheated to 65° C., followed by 2 times 3 min in Wash buffer and dehydration in a series of 70%, 85%, and 96% ethanol. After air drying, the slide was mounted with 15 µL of Vectashield H-1000 (Vector Laboratories, Inc. Burlingame) supplemented with 0.1 µg/mL 4,6-diamidino-2-phenylindole (DAPI, Sigma Chemicals) and sealed with a cover slip. Detection was performed within a week after hybridization using a Leica or an Olympus BX G1 fluorescence microscope, equipped with DAPI, FITC, TRITC and FITC/TRITC double-pass and DAPI/FITC/TRITC triple filters under 100× oil objective.

Figure 5:
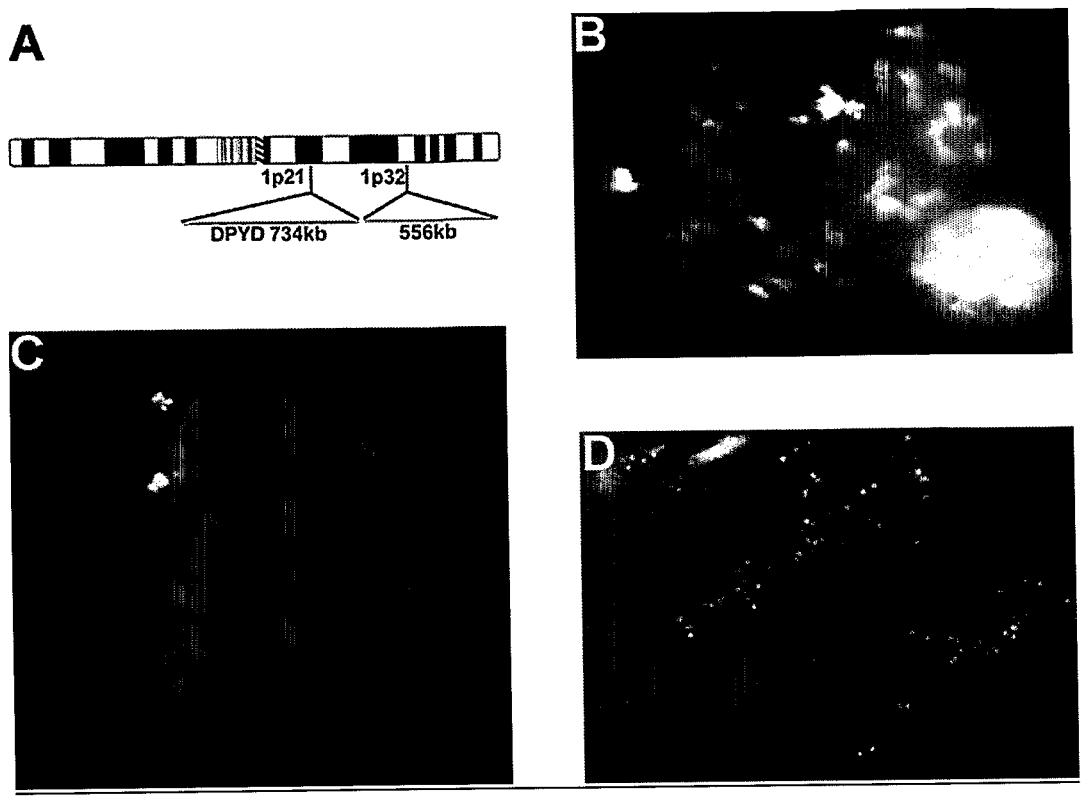
FIG. 5 illustrates the hybridization of DPYD and a locus specific DNA probe located on the same arm telomeric to DPYD (reference probe). (A) shows the area covered by the DPYD and reference probes, respectively. Hybridization of the probes to metaphase spreads from (B) normal pheripheral blood cells or (C) chemo sensibility breast cancer cell line BT20 and (D) to tumor tissue.

FIG. 5 shows hybridization of DPYD (Dihydropyrimidine dehydrogenase) to metaphase chromosomes. (A) Drawing of the area covered by the probes; (B) Hybridization of the DPYD probes to metaphase spreads from normal peripheral blood. Two normal chromosomes 1 are represented by having a red and a green signal located on the same chromosome. Hybridization of the DPYD probe to nuclei shows two red signals and two green signals. Reference probe as a locus specific DNA probe located on the same arm telomeric to the DPYD gene of interest; (C) Hybridization of the DPYD probe to metaphase spreads from the chemo sensibility breast tumor cell line BT-20. Two normal chromosome 1 are represented by having a red and green signal located on the same chromosome. (D) Hybridization of the DPYD probe to tissue, giving a ratio between the red signal and green signal of 0.49, indicate a deletion of the DPYD gene.

Figure 6:
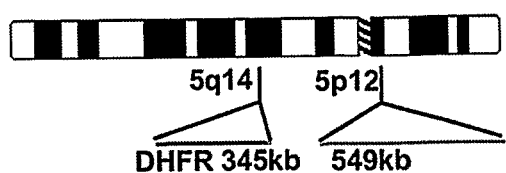
FIG. 6 illustrates the hybridization of DHFR and a locus specific DNA probe located on the opposite arm as the DHFR gene (reference probe). (A) shows the area covered by the. Hybridization of the probes to metaphase spreads from (B) normal peripheral blood cells or (C) chemo sensibility breast cancer cell line BT20 and (D) to tumor tissue.
Figure 6:
Figure 6:
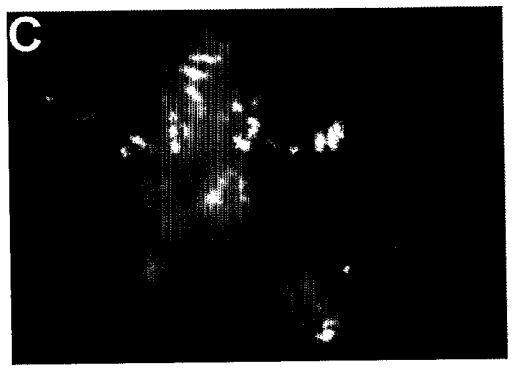
Figure 6:
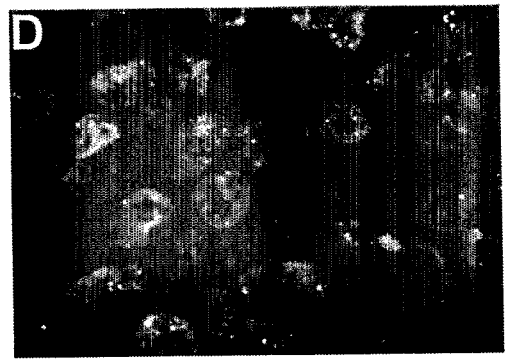

FIG. 6 shows hybridization of DHFR (Dihydrofolate reductase) to metaphase chromosomes. (A) Drawing of the area covered by the probes; (B) Hybridization of the DHFR probes to metaphase spreads from normal peripheral blood. Two normal chromosomes 5 are represented by having a red and a green signal located on the same chromosome. Hybridization of the DHFR probe to nuclei shows two red signals and two green signals. Reference probe as a locus specific DNA probe is located on the opposite arm as the DHFR gene of interest; (C) Hybridization of the DHFR probe to metaphase spreads from the chemo sensibility breast tumor cell line BT-20. Two normal chromosome 5 are represented by having a red and green signal located on the same chromosome; (D) Hybridization of the DHFR probe to tissue, giving a ratio between the red signal and green signal of 0.76, indicate a deletion of the DHFR gene.

Figure 7:
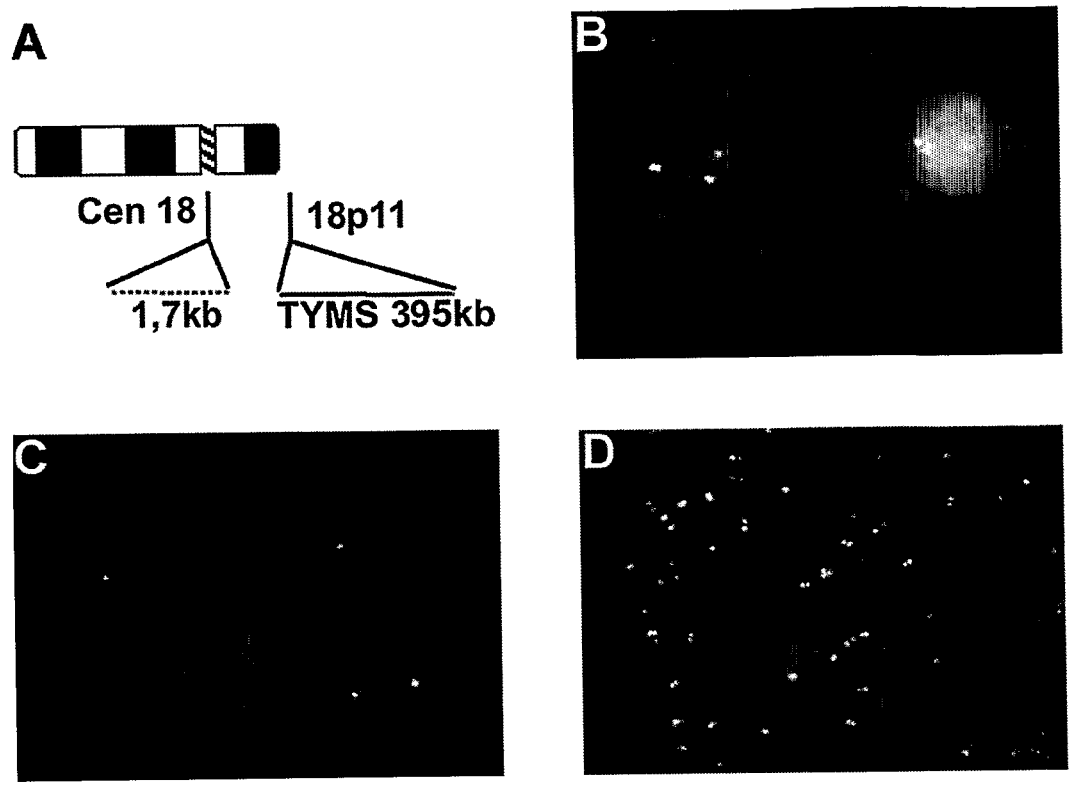
FIG. 7 illustrates the hybridization of TYMS and a centromeric specific DNA/PNA probe located on the same chromosome as the TYMS gene (reference probe). (A) shows the area covered by the. Hybridization of the probes to metaphase spreads from (B) normal pheripheral blood cells or (C) chemo sensibility breast cancer cell line BT20 and (D) to tumor tissue.

FIG. 7 shows hybridization of TYMS (Thymidylate synthase) to metaphase chromosomes. (A) Drawing of the area covered by the probes; (B) Hybridization of the TYMS probes to metaphase spreads from normal peripheral blood. Two normal chromosomes 18 are represented by having a red and a green signal located on the same chromosome. Hybridization of the TYMS probe to nuclei shows two red signals and two green signals. Reference probe as a centromeric specific DNA/PNA probe located on the same chromosome as the TYMS gene of interest; (C) Hybridization of the TYMS probe to metaphase spreads from the chemo sensibility breast tumor cell line BT-20. Two normal chromosome 5 are represented by having a red and green signal located on the same chromosome; (D) Hybridization of the TYMS probe to tissue, giving a ratio between the red signal and green signal of 0.95, indicating a normal copy number.

Figure 8:
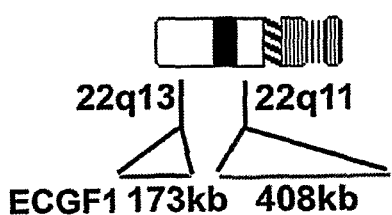
FIG. 8 illustrates the hybridization of ECGF1 and a locus specific DNA probe located on the same arm centromeric to the ECGF1 gene (reference probe). (A) shows the area covered by the. Hybridization of the probes to metaphase spreads from (B) normal pheripheral blood cells or (C) chemo sensibility breast cancer cell line BT20 and (D) to tumor tissue.
Figure 8:
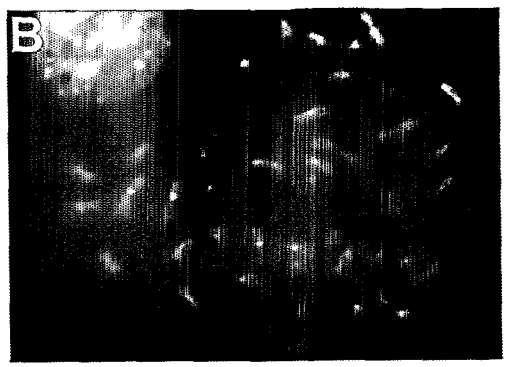
Figure 8:
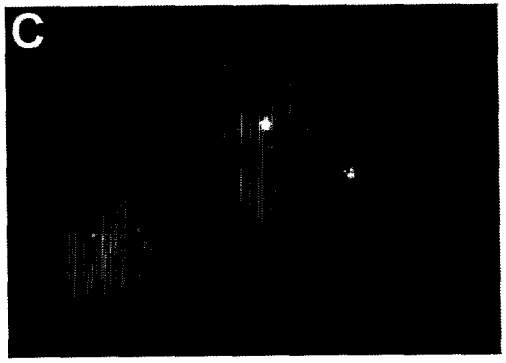
Figure 8:
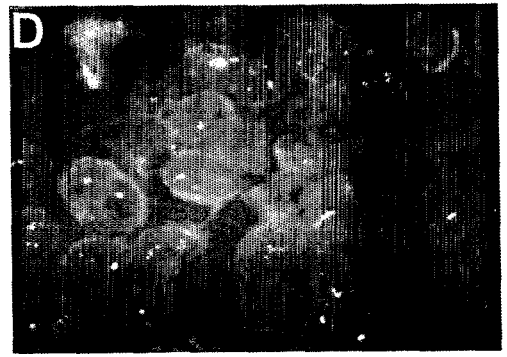

FIG. 8 shows hybridization of ECGF1 (Thymidine phosphorylase) to metaphase chromosomes. (A) Drawing of the area covered by the probes; (B) Hybridization of the ECGF1 probes to metaphase spreads from normal peripheral blood. Two normal chromosomes 22 are represented by having a red and a green signal located on the same chromosome. Hybridization of the ECGF1 probe to nuclei shows two red signals and two green signals. Reference probe as a locus specific DNA probe located on the same arm centromeric to the ECGF1 gene of interest; (C) Hybridization of the ECGF1 probe to metaphase spreads from the chemo sensibility breast tumor cell line BT-20. Two normal chromosome 22 are represented by having a red and green signal located on the same chromosome. (D) Hybridization of the ECGF1 probe to tissue, giving a ratio between the red signal and green signal of 2.89, indicate an amplification of the ECFG1 gene.

Example 2

Predictive Assay for the Outcome of 5-FU Treatment in Breast Cancer

Background: A clinical utilizable predictive marker for the clinical outcome of 5-FU containing treatment has not been developed. The efficacy of 5-FU is mediated through a functioning thymidylate synthase pathway and ought to be blocked by absence or reduced function of key enzymes in the pathway. We used fluorescence in situ hybridization (FISH) to identify copy number changes in four candidate genes from the thymidylate cycle.

Material and Methods:

Patient population: Based upon patient registration records at the Departments of Oncology at Rigshospitalet and Herlev University Hospital, patients who started treatment with capecitabine between 1998 and 2004 for metastatic breast cancer were identified. The participating team of oncologists undertook an on-site review of all patient source records. Two groups of patients were selected: One group without clinical benefit (disease progression in less than 3 months) and a second group with clinical benefit (time to progression above 6 months). Archival tissue from the primary tumor of 35 patients was collected. No tumor area could be identified in the tissue received from 6 of these patients.

The remaining 29 patients were analyzed for gene copy number (GCN) changes by FISH technique in the 4 of the genes (TYMS, DHFR, TP=ECGF1 and DPD) involved in the primary incorporation of 5-FU into DNA.

The therapeutic regimen: Treatment with capecitabine (Xeloda®) was administered according to predetermined flow sheets and recommendations. Capecitabine 1250 mg/m² was given orally two times daily on day 1 to 14 every 3 weeks. Treatment was continued until disease progression, severe toxicity, patient refusal, or a maximum of one year. Severe toxicity requiring treatment discontinuation included increase of bilirubin >10× upper limit of normal (ULN) or increase of transaminases ≥20×ULN; or any severe or life threatening adverse event. Treatment was postponed one week if leukocyte count was ≤3.0×10⁹/l or platelets≤100× 10⁹/l. The WHO toxicity criteria grading system was used. The dose of capecitabine was decreased by 25% following stomatitis grade 1, by 50% following stomatitis grade 2 and was stopped permanently following grade 3 stomatitis. Following grade 1 hand-foot syndrome the dose of capecitabine was decreased 25%, and following grade 2 hand-foot skin reaction capecitabeine was discontinued until recovery and a 50% dose reduction was then mandatory. Following diarrhea grade 1-2 the patient was treated with Imodium and the dose of capecitabine was reduced by 50%. Treatment was stopped permanently following grade 3-4 diarrhea.

Patient classification, data collection and statistical methods: Pre-treatment investigations performed within 4 weeks of therapy initiation included full history and physical examination, complete blood cell count (CBC), serum chemistry, chest X-ray, bone scan or bone X-rays and site-specific imaging as appropriate. CBC counts were obtained on day 1 of each cycle and serum chemistry was performed every 3 cycles. The primary and predefined endpoint of the analysis was clinical benefit (CB) categorized as good CB, uncertain CB, and no CB. Good CB was defined as progression-free survival (PFS) of 6 months or more, no CN was defined as PFS of 3 months or less, and uncertain PFS was defined as PFS of more than 3 months but less than 6 months. PFS was calculated as the time from initiation of capecitabine disease progression or death using WHO criteria. The two sided p-value was calculated using Exact test for hypergeometric distribution.

FISH analysis: The FISH assay was performed according to the method described in example 1 and in the Detailed Description of Invention. The ratio between red and green signals was evaluated by FISH on 29 patient samples containing tumor cells. A total of 60 cells were counted per patient, and only cells containing both one red and one green signal were evaluated. The tumor tissue was screened, and counting was performed in the area with the most pronounced deviation from the ratio 1 was selected for evaluation. Signals of the same color with a distance less than or equal to the diameter of the signals were evaluated as one. As for HER2 and TOP2A FISH pharmDx™ Kit, a ratio below 0.8 is considered a deletion while a ratio over 2.0 is considered as amplification. Ratios between 0.8 and 2.0 are considered normal.

IHC analysis for TS: The TS protein was evaluated by standard IHC methods using Dako antibody according to the manufacture's recommendations.

TABLE 1

Patients Characteristics (At Primary Diagnosis)

|  | Total | | Clinical benefit | | No clinical benefit | |
| --- | --- | --- | --- | --- | --- | --- |
|  | No. | % | No. | % | No. | % |
| Eligible patients | 24 | 100 | 15 | 63 | 9 | 37 |
| Age at operation (years) | | | | | | |
| Median | 51 | | 50 | | 51 | |
| Range | 34-76 | | 34-76 | | 35-75 | |
| Tumor size | | | | | | |
| Median | 23 | | 15 | | 25 | |
| Range | 8-80 | | 8-60 | | 20-80 | |
| Malignancy | | | | | | |
| Grade I | 4 | 17 | 3 | 20 | 1 | 11 |
| Grade II | 7 | 29 | 4 | 27 | 3 | 33 |

TABLE 1-continued

Patients Characteristics (At Primary Diagnosis)

|  | Total | | Clinical benefit | | No clinical benefit | |
| --- | --- | --- | --- | --- | --- | --- |
|  | No. | % | No. | % | No. | % |
| Grade III | 8 | 33 | 4 | 27 | 4 | 44 |
| Non-ductal or unknown | 5 | 21 | 4 | 27 | 1 | 11 |
| Hormone receptor status | | | | | | |
| Positive (ER or PgR) | 9 | 38 | 7 | 47 | 3 | 33 |
| Negative | 10 | 42 | 5 | 33 | 4 | 44 |
| Unknown | 5 | 21 | 3 | 20 | 2 | 22 |
| Adjuvant CMF | 9 | 38 | 5 | 33 | 4 | 44 |

Results: Tissue specimens of the 35 patients were collected and analyzed for copy number changes by the FISH assays for the four genes involved in the primary incorporation of 5-FU into DNA: TYMS, TP, DHFR, and DPD. The technical details are described in Example 1. Tumor tissue was not identified in the tissue blocks obtained from 6 patients and in 5 cases the FISH analysis was unsuccessful for at least 3 of the genes or the patients did not fulfill the inclusion criteria. The FISH analysis was successful for 24 patients, see Table 2 below. Patient 1 to 15 had UP longer than 6 months while patient 16 to 24 had TTP shorter than 3 months.

From Table 2 it is clear that the DPD assay cannot serve to predict the clinical outcome of the 5-FU treatment as 8 of 15 patients (53%) with clinical response had a deletion of the DPD gene while 6 of 9 patients (67%) resistant to 5-FU treatment had a deletion. Totally, 14 of 24 patients (58%) showed a DPD deletion. However, the ratios based on the other 3 FISH assays show a clearly non-random distribution. A total of 15 patients had a clinical benefit (TTP>6 months) of the 5-FU treatment. All 15 patients had normal gene copy number of the 3 genes TYMS, TP, and DHFR. A total of 9 patients had no clinical benefit (TTP_<3 months). Seven of these patients had deletion of at least one of the 3 genes. This distribution (Table 3) is highly significant (p=0.002).

TABLE 2

Ratios of the four GCN assays using a chromosome specific reference located on the same chromosome as the target gene.

| Patient | TYMS | DHFR | TP | DPD |
| --- | --- | --- | --- | --- |
| 1 | 0.92 | 1.13 | 1.02 | 0.60 |
| 2 | 0.99 | 1.14 | 1.04 | 0.68 |
| 3 | 0.98 | 1.08 | 1.00 | 0.76 |
| 4 | 0.96 | 1.20 | 1.06 | 0.92 |
| 5 | 1.02 | 1.14 | 0.97 | 0.85 |
| 6 | 0.86 | 1.11 | 1.01 | 0.88 |
| 7 | 1.08 | 1.07 | 0.93 | 0.73 |
| 8 | 0.94 | 1.41 | 0.84 | 0.76 |
| 9 | 0.96 | 1.14 | 0.92 | 0.54 |
| 10 | 0.99 | 1.10 | 0.98 | 0.79 |
| 11 | 0.91 | 0.96 | 1.03 | 0.93 |
| 12 | 0.95 | 1.03 | 1.06 | 0.84 |
| 13 | 0.86 | | 0.89 | 0.86 |
| 14 | 0.94 | 1.10 | 1.71 | 0.68 |
| 15 | 1.01 | 1.10 | 1.06 | 0.99 |

TABLE 2-continued

Ratios of the four GCN assays using a chromosome specific reference located on the same chromosome as the target gene.

| 16 | 0.59 | 1.01 | | 0.77 |
|---|---|---|---|---|
| 17 | 0.90 | 1.16 | 1.03 | 0.93 |
| 18 | 1.00 | 0.46 | 0.99 | 0.95 |
| 19 | 0.76 | 1.49 | 0.58 | 0.69 |
| 20 | 0.99 | 0.76 | 0.43 | 0.95 |
| 21 | 0.99 | 0.81 | 0.96 | 0.77 |
| 22 | 0.53 | 1.21 | 0.90 | 0.50 |
| 23 | 0.81 | 0.77 | 0.95 | 0.73 |
| 24 | 1.02 | 0.74 | 0.34 | 0.49 |
| Norm | 0.93 | 1.02 | 0.96 | 1.04 |

The color code:
White = normal, ratio 0.8-2.0;
Green = deletion, ratio <0.8;
red = amplification, ratio >2.0

The TS protein expression was evaluated by IHC. With respect to protein level the patients were randomly distributed in the two clinical outcome groups.

TABLE 3

Distribution of normal and abnormal GCNs in relation to clinical benefit.

| | Normal copy number of all 3 genes (TYMS, DHFR, TP) | Abnormal copy number of at least 1 of the 3 genes | Total |
|---|---|---|---|
| Clinical Benefit | 15 (100%) | 0 (0%) | 15 (62.5%) |
| No Clinical Benefit | 2 (22%) | 7 (78%) | 9 (37.5%) |
| Total | 17 (71%) | 7 (29%) | 24 (100%) |

Nine of the patients analyzed previously received 5-FU containing adjuvant treatment. Five of these had a TTP longer than 6 months and a normal GCN. Of the four patients with TTP shorter than 3 months, two had normal GCN and two abnormal.

Discussion: These preliminary data shows that a 3 gene FISH assay (TYMS, DHFR and TP) can predict resistance to 5-FU treatment. The resistance is associated with deletion of at least one of the genes. The resistant genotype was identified in the primary tumor and resistance to 5-FU therapy seems to be highly preserved. Thus, resistance is a feature present in the tumor cells before initiating 5-FU treatment, and therefore not a feature acquired during (or as a consequence of) treatment. In this series of patients the TP genes status did not add any information to the predictive value, and this gene could have been omitted from the analysis. However, this observation will be confirmed in a larger series of patients including analysis of all 4 genes in addition to the TK and MTHFR genes. This study is the first observation of gene deletions in the 5-FU pathway.

TS protein assessed by IHC did neither correlate to genes status nor clinical outcome.

Example 3

Probes for 5-FU, MTX and Combinatorial Treatment Containing 5-FU and MTX, e.g. CMF Treatment Fish Probes:
1. TYMS (Thymidylate synthase) on 18p11.32
2. TP (ECGF1) (Thymidine phosphorylase) on 22q13.32
3. DPD (DPYD) (Dihydropyrimidine dehydrogenase) on 1p22
4. DHFR (Dihydrofolate reductase) on 5q11.2-q13.2
5. TK1 (Thymidine kinase) at 17q25.2-q25.3
6. MTHFR (Methylenetetrahydrofolate reductase) at 1p36.3
7. ERCC1 (excision repair cross-complementing 1) on 19q13.2
8. XPD (Xeroderma Pigmentosum gene D)

Thymidine kinase (TK1 alias TK) catalyses the phosphorylation of thymidine to deoxythymidine monophosphate. The gene is located at 17q25.2-q25.3. The gene contains many non-coding inserts and numerous alu sequences. Nucleotide sequencing indicated considerable evolutionary conservation of the TK gene. Sequencing of the entire 12.9 kb human TK gene (Flemmington 1987) and flanking regions showed the TK gene is composed of 7 exons. In the 5-prime flanking region of the TK gene (Sauve 1990) a position of nucleotides sequences are located that can act as binding site for transacting factors as well as potential cis-acting sequences. The latter were compared with those of the promoter of the human PCNA gene. Both TK and PCNA are maximally expressed at the G1/S boundary of the cell cycle.

Intracellular folate homeostasis depends on 5,10-methylenetetrahydrofolate reductase (MTHFR), a critical enzyme in folate metabolism that catalyses the irreversible conversion of 5-methyltetrahydrofolate. The substrate 5,10-methylenetetrahydrofolate is required for DNA synthesis and for maintaining the balance of the nucleotide pool, whereas 5-methyltetrahydrofolate is required for methylation reactions, including the methylation of homocysteine to methionine and the maintenance of DNA methylation patterns. (OMIM, 607093).

A C677T polymorphism has been proposed to modulate the cytotoxic effect of 5-FU and MTX (Methotrexate) because the modes of action of 5-FU and MTX are critically depended on the cellular composition of folates. Sohn et al. (2004) showed that cell lines with mutant C677T MTHFR had decreased MTHFR activity, changed intracellular folate distribution, accelerated growth rate, and increased TYMS activity. In two cell lines from breast and colon cancer, respectively, the C677T mutation increased chemo sensitivity to 5-FU, but decreased the chemo sensitivity of the breast cell line to MTX. Based on these preliminary observations in vitro, we propose the CNC (copy number changes) of the MTHFR and TK genes are predictive for patient outcome when treated with 5-FU, MTX or combinatory regiments containing these drugs, e.g. CMF treatment.

TABLE 4

OMIM taxonomy of breast cancer specific markers mentioned in the text.

| Gene locus | Gene | Protein | Function | Alternative names |
|---|---|---|---|---|
| 1p36.3 | MTHFR | Methylenetetrahydrofolate reductase | Folate metabolism, cofactor to DHFR | |
| 1p22 | DPYD | Dihydropyrimidine Dehydrogenase | Initial and rate-limiting enzyme in uracil and thymidine catabolism | DHP; DPD |

TABLE 4-continued

OMIM taxonomy of breast cancer specific markers mentioned in the text.

| Gene locus | Gene | Protein | Function | Alternative names |
|---|---|---|---|---|
| 1q43 | MTR | 5-Methyltetrahydrofolate-homocysteine methyltransferase | Converts N5-methyltetrahybrofolate into tetrahydrofolate | MTR |
| 5q11.2 | DHFR | Dihydrofolate reductase | Converts dihydrofolate into tetrahydrofolate | CG14887; CT34709 |
| 8q24.12-q24.13 | MYC | | Oncogene | c-myc |
| 9p21 | CDKN2 | Cyclin-dependent kinase inhibitor 2A | Involved in inversions, translocations and deletions | p16; p19; p14; TP16; MST1 |
| 11q13 | CCND1 | Cyclin D1 | | Cyclin D1; Prad1; BCL1 |
| 16q22.1 | CDH1 | E-cadherin | | CADHERIN1 |
| 17p13.1 | TP53 | p53 | Transformation related protein 53 | TRP53 |
| 17q25.2-q25.3 | TK1 | Thymidine kinase | Catalyzes the phosphorylation of thymidine to deoxythymidine | TK |
| 17q21 | ERBB2 | HER2 | Receptor | Her-2/neu |
| 17q21 | TOP2A | topoIIα | Topoisomerase | TOP2 |
| 18p11.32 | TYMS | Thymidylate synthase | | TS; TMS dTMP synthase |
| 19q13.2 | ERCC1 | Excision repair cross-complementing 1 gene | DNA repair gene | UV20 |
| 19q13.2-q13.3 | XPD | Xeroderma Pigmentosum group D | DNA repair gene | XP, XPCD. TTD1, XPH |
| 22q13 | TP | Thymidine phosphorylase | Reversible dephosphorylation of thymidine and analogs | ECGF1, platelet derived endothelial cell growth factor |
| Centromere 2 and 10 | Repeat | Ploidy assessment | Aneuploidy level of the tumor | Alpha repeat unit |

Example 4

Similar Study on Colon Cancer and Head & Neck Cancer or Other Cancer Types

Retrospective studies using the kit comprising probes for genes from the 5-FU pathway are under planning based on clinical trials and patients series with colorectal and head and neck cancer. One such trial is a neoadjuvant trial in patients with tumors in the oral cavity, oropharynx, hypopharynx and larynx that were randomized to loco regional therapy alone versus three courses of cisplatin and 5-FU followed by loco regional therapy. Archival tumor tissue has been retrieved from patients that previously received adjuvant 5-FU according to the Mayo-regimen following completely resected colorectal cancer. The patients have been analyzed with IHC for TS expression showing no predictive value of the TS protein expression (ASCO 2005 abstract). An evaluation of predictive value of the kit comprising probes for genes from the 5-FU pathway is under planning. Both studies are expected to show correlation between clinical outcome and GCN changes in the 5-FU pathway.

Example 5

Study of Adjuvant Breast Cancer (Protocol 77-B and Protocol 82-C)

The Danish Breast Cancer Cooperative Group (DBCG) has conducted two large randomized trials that documenting the efficacy of CMF (cyclophasphamide, methotrexate and 5-fluorouracil). DBCG trial 77-B included premenopausal patients with invasive breast cancer and a primary tumor larger than 5 cm resected by mastectomy or pathologically involved auxiliary nodes excised at auxiliary dissection. No locally advanced breast cancer or distant disease was allowed. Patients in DBCG 77-B were randomized to radiotherapy alone (N=287) or radiotherapy in combination with either single agent cyclophosphamide (N=424) or CMF (N=432). DBCG trial 82-C included postmenopausal patients with otherwise similar inclusion criteria's, e.g. operable breast cancer and either s primary tumor larger than 5 cm or positive auxiliary nodes. Patients in DBCG trial 82-C were randomized to one year of tamoxifen (N=432) or tamoxifen plus CMF (N=432). The predictive value of the kit comprising probes for genes from the 5-FU pathway will be quantified by the hazard ratio in a Cox Proportional Hazards regression analysis. These two randomized trial are expected to extend the observations outlined in example 2 for 5-FU monotherapy to also include the 5-FU containing combinatory treatment, CMF.

Example 6

Kit Design with Different Reference Probes

Alternative design of the kit for detection of levels of the genes in the 5-FU pathway will be explored. In example 2 four reference probes, each located on the same chromosome as the target genes, was used. It will be tested whether this approach can be substituted by other kit designs without loss of diagnostic specificity and sensitivity. Using centromere 18 decreases the diagnostic sensitivity, and other centromere probes, preferable centromere 2 and centromere 10 will be tested.

TABLE 5

Ratios of the four GCN assays using chromosome 18 reference probe.

| Patient | TYMS | DHFR | TP | DPD |
|---|---|---|---|---|
| 1 | 0.92 | 1.36 | 1.20 | 0.76 |
| 2 | 0.99 | 1.41 | 1.37 | 0.96 |
| 3 | 0.98 | 0.88 | 0.86 | 0.88 |
| 4 | 0.96 | 1.98 | 1.54 | 1.01 |
| 5 | 1.02 | 1.50 | 0.83 | 0.74 |
| 6 | 0.86 | 1.62 | 1.17 | 1.05 |
| 7 | 1.08 | 1.18 | 1.61 | 1.22 |
| 8 | 0.94 | 0.94 | 0.79 | 1.03 |
| 9 | 0.96 | 0.93 | 0.79 | 0.56 |
| 10 | 0.99 | 1.05 | 1.01 | 1.10 |
| 11 | 0.91 | 1.00 | 1.41 | 1.60 |
| 12 | 0.95 | 1.04 | 0.67 | 0.82 |
| 13 | 0.86 |  | 0.82 | 0.69 |
| 14 | 0.94 | 0.84 | 0.98 | 0.65 |
| 15 | 1.01 | 0.74 | 0.73 | 0.71 |
| 16 | 0.59 | 1.19 |  | 0.91 |
| 17 | 0.90 | 1.04 | 0.66 | 0.85 |
| 18 | 1.00 | 0.54 | 1.91 | 0.95 |
| 19 | 0.76 | 1.14 | 0.44 | 0.61 |
| 20 | 0.99 | 1.24 | 1.10 | 1.11 |
| 21 | 0.99 | 1.10 | 0.73 | 0.76 |
| 22 | 0.57 | 1.23 | 0.89 | 0.49 |
| 23 | 0.81 | 0.94 | 1.16 | 1.40 |
| 24 | 1.02 | 0.94 | 1.02 | 1.19 |
| Norm | 0.93 | 0.95 | 0.99 | 0.96 |

The DPD gene distributes different compared to the one seen in example 2: Seven of 15 patients (47%) with clinical response had a deletion of the DPD gene while 3 of 9 patients (33%) resistant to 5-FU treatment had a deletion. Totally, 10 of 24 patients (42%) showed a DPD deletion.

TABLE 6

Distribution of normal and abnormal gene copy numbers in relation to clinical benefit using centromere 18 as reference.

|  | Normal copy number of all 3 genes (TYMS, DHFR, TP) | Abnormal copy number of at least 1 of the 3 genes | Total |
|---|---|---|---|
| Clinical Benefit | 11 (73%) | 4 (27%) | 15 (62.5%) |
| No Clinical Benefit | 3 (33%) | 6 (67%) | 9 (37.5%) |
| Total | 14 (58%) | 10 (42%) | 24 (100%) |

The distribution is not significant (p=0.20). Neither inclusion of the DPD gene nor exclusion of the TP gene will result in a significant pattern of distribution. Alternative references will be tested, and the required minimum number of reference probes will be determined.

Example 7

Gene Copy Number Changes for 5-FU Resistance in Colorectal Cancer

A 41 years old patient received after complete resection of a Duke's B colon carcinoma adjuvant treatment with 5-fluorouracil (5-FU) and isovorin. The treatment was according to the Mayo regimen, which included bolus infusion of 5-FU (425 mg/m$^2$) and isovorin (10 mg/m$^2$) for 5 days, repeated every 4 weeks, for a total of 6 cycles. Fourteen and a half month after initiation of adjuvant treatment the patient got a relapse of the disease and subsequently the patients died 4 months later. Apparently, treatment failed. This may be due to therapy resistance to 5-FU.

Retrospectively tumor tissue was analyzed for gene copy number (GCN) changes by FISH using probes for 3 genes (DHFR, TYMS and TP), cf Example 1, involved in the primary incorporation of 5-FU into DNA. FISH procedure was performed according to the method described in Example 1. Each of the markers was determined separately.

As described in Example 1 and 2 the ratio between red and green signals was evaluated. A total of 60 tumor cells were counted, and only cells containing both one red and one green signal was evaluated. The tumor tissue was screened and the area with most pronounced deviation from the ration 1 was selected for evaluation. The TP gene/chromosome ratio in the tumor cells was below 0.8 indicating a deletion of the TP gene. This observation strongly suggests a correlation with 5-FU treatment failure.

Example 8

Gene Copy Number Changes for 5-FU Resistance in Head a Neck Cancer

A patient in the early sixties with metastatic head and neck cancer was treated with 5-fluorouracil (5-FU) infusion at a dose of 1000 mg/m$^2$ per 24 hours. The total infusion time was 120 hours. After one and a half month the treatment respond was evaluated and the patient was found to have progressive disease. Following progression on 5-FU, cisplatin at a dose of 100 mg/m$^2$ was administered i.v. to the patient. The treatment with 5-FU and cisplatin were repeated every third week for a maximum of ten cycles or until progressive disease or unacceptable to toxicity. After another 2 month on treatment with cisplatin the patient died. Apparently, treatment failed. This may be due to therapy resistance.

Retrospectively tumor tissue was analyzed for gene copy number (GCN) changes by FISH using probes for 3 genes (DHFR, TYMS and TP), cf. Example 1, involved in the primary incorporation of 5-FU into DNA. FISH procedures were performed according to the method described in Example 1. Each probe was tested separately.

As described in Examples 1 and 2 the ratio between red and green signals was evaluated. A total of 60 tumor cells were counted, and only cells containing both one red and one green signal was evaluated. The tumor tissue was screened and the area with most pronounced deviation from the ration 1 was selected for evaluation. The TYMS gene/chromosome ratio in the tumor cells was below 0.8 indicating a deletion of the TYMS gene which strongly suggests a correlation with 5-FU treatment failure.

Example 9

Distribution of Normal and Abnormal Gene Copy Number in Colorectal Cancer and Head & Neck Cancer The distribution of normal and abnormal gene copy numbers was investigated for a large group of patients suffering from colorectal cancer or head & neck cancer, respectively. FISH procedures were conducted as described in Examples 1 and 2. Reference probes used for MTR, MTHFR and TK1 were PNA probes specific for centromer regions on chromosome 1 (MTR and MTHFR) and 17 (TK1), respectively. The MTR probe used was a DNA probe binding to a region located on chromosome 1q43. The results are shown in Tables 7, 8 and 9.

TABLE 7

Distribution of normal and abnormal gene copy numbers in colorectal cancer

|  | Normal copy number | Deleted | Amplified |
|---|---|---|---|
| DHFR | 232 | 8 | 0 |
| TP | 317 | 31 | 0 |
| TYMS | 325 | 17 | 0 |
| TK1 | 33 | 1 | 1 |
| MTHFR | 36 | 0 | 0 |
| MTR | 19 | 0 | 0 |

When using a cut-off of 0.8 for a deletion and 2.0 for amplification, 8 of 218 patients (3.7%) had deletion of DHFR gene. Twenty nine of 299 patients (9.7%) had deletion of TP. Seventeen of 302 patients (5.6%) had deletions of TYMS. One of 34 patients (2.9%) had deletion and 1 had amplification of TK1, while no deletions of MTHFR and MTR were detected.

TABLE 8

Distribution of normal and abnormal GCNs in Head & Neck cancer

|  | Normal copy number | Deleted | Amplified |
|---|---|---|---|
| DHFR | 34 | 3 | 0 |
| TP | 32 | 4 | 0 |
| TYMS | 25 | 1 | 0 |

When using a cut-off of 0.8 for a deletion and 2.0 for amplification, 3 of 37 patients (8.1%) had deletion of DHFR gene. Four of 36 patients (11%) had deletion of TP, while 1 deletion of 26 patients (3.8%) was detected for TYMS.

Distribution of normal and abnormal gene copy numbers for head & neck and colorectal cancer is shown in Table 9. Eight of 27 patients with head & neck cancer (29.6%) had deletion in at least 1 of the 3 genes (TYMS, DHFR, TP) whilst 48 of 284 patients with colorectal cancer (16.9%) had deletion of at least 1 of 3 genes. For both cancers the total number is patients with normal copy number in all 3 genes or with deletion of at least 1 of the 3 genes.

TABLE 9

|  | Normal copy number of all three genes (TYMS, DHFR, TP) | Abnormal copy number of at least 1 or 3 genes (TYMS, DHFR, TP) | Total |
|---|---|---|---|
| Head & neck | 19 (70.4%) | 8 (29.6%) | 27 (100%) |
| Colorectal cancer | 236 (83.1%) | 48 (16.9%) | 284 (100%) |

REFERENCES

1. Efficacy of adjuvant fluorouracil and folinic acid in colon cancer. International Multicentre Pooled Analysis of Colon Cancer Trials (IMPACT) investigators Lancet 1995; 345: 939-44.
2. Effects of chemotherapy and hormonal therapy for early breast cancer on recurrence and 15-year survival: an overview of the randomised trials Lancet 2005; 365:1687-717.
3. Ingvarsson S. Molecular genetics of breast cancer progression. Semin Cancer Biol 1999; 9:277-88.
4. Thorlacius S, Thorgilsson B, Bjornsson J et al. TP53 mutations and abnormal p53 protein staining in breast carcinomas related to prognosis. Eur J Cancer 1995; 31A:1856-61.
5. Overgaard J, Yilmaz M, Guldberg P, Hansen L L, Alsner J. TP53 mutation is an independent prognostic marker for poor outcome in both node-negative and node-positive breast cancer. Acta Oncol 2000; 39:327-33.
6. Geisler S, Lonning P E, Aas T et al. Influence of TP53 gene alterations and c-erbB-2 expression on the response to treatment with doxorubicin in locally advanced breast cancer. Cancer Res 2001; 61:2505-12.
7. Mouridsen, H. T., Andersen, J, Andersson, M., Dombernowsky, P., Ejlertsen, B., Rose, C., Sorensen, P. G., Sandberg, E., Andersen, K. W., Jensen, M. B., Bengtson, N. O., Berg, J., and Nordenskjöld, B. Adjuvant anthracycline in breast cancer. Improved outcome in premenopausal patients following substitution of methotrexate in the CMF combination with epirubicin. Proc Am Soc Clin Oncol 18, 68a. 1999. Ref Type: Abstract
8. Knoop A S, Knudsen H, Balslev E et al. Retrospective analysis of topoisomerase IIa amplifications and deletions as predictive markers in primary breast cancer patients randomly assigned to cyclophosphamide, methotrexate, and fluorouracil or cyclophosphamide, epirubicin, and fluorouracil: Danish Breast Cancer Cooperative Group. J Clin Oncol 2005; 23:7483-90.
9. Berger J M, Gamblin S J, Harrison S C, Wang J C. Structure and mechanism of DNA topoisomerase II. Nature 1996; 379:225-32.
10. Coukell A J, Faulds D. Epirubicin. An updated review of its pharmacodynamic and pharmacokinetic properties and therapeutic efficacy in the management of breast cancer. Drugs 1997; 53:453-82.
11. Muss H B, Thor A D, Berry D A et al. c-erbB-2 expression and response to adjuvant therapy in women with node-positive early breast cancer. N Engl J Med 1994; 330:1260-1266.
12. Thor A D, Berry D A, Budman D R et al. erbB-2, p53, and efficacy of adjuvant therapy in lymph node-positive breast cancer. J Natl Cancer Inst 1998; 90:1346-60.
13. Clahsen P C, van de Velde C J, Duval C et al. p53 protein accumulation and response to adjuvant chemotherapy in premenopausal women with node-negative early breast cancer. J Clin Oncol 1998; 16:470-479.
14. Paik S, Bryant J, Tan-Chiu E et al. HER2 and choice of adjuvant chemotherapy for invasive breast cancer: National Surgical Adjuvant Breast and Bowel Project Protocol B-15. J Natl Cancer Inst 2000; 92:1991-98.
15. Di Leo A, Larsimont D, Gancberg D et al. HER-2 and topo-isomerase IIalpha as predictive markers in a population of node-positive breast cancer patients randomly treated with adjuvant CMF or epirubicin plus cyclophosphamide. Ann Oncol 2001; 12:1081-89.
16. Järvinen T A, Tanner M, Rantanen V et al. Amplification and deletion of topoisomerase IIalpha associate with ErbB-2 amplification and affect sensitivity to topoisomerase II inhibitor doxorubicin in breast cancer. Am J Pathol 2000; 156:839-47.
17. Coon J S, Marcus E, Gupta-Burt S et al. Amplification and overexpression of topoisomerase IIalpha predict response to anthracycline-based therapy in locally advanced breast cancer. Clin Cancer Res 2002; 8:1061-67.
18. Di Leo A, Gancberg D, Larsimont D et al. HER-2 amplification and topoisomerase IIalpha gene aberrations as predictive markers in node-positive breast cancer patients randomly treated either with an anthracycline-based therapy or with cyclophosphamide, methotrexate, and 5-fluorouracil. Clin Cancer Res 2002; 8:1107-16.

19. Park K, Kim J, Lim S, Han S. Topoisomerase II-alpha (topoII) and HER2 amplification in breast cancers and response to preoperative doxorubicin chemotherapy. Eur J Cancer 2003; 39:631-34.
20. Harris L N, Yang L, Liotcheva V et al. Induction of topoisomerase II activity after ErbB2 activation is associated with a differential response to breast cancer chemotherapy. Clin Cancer Res 2001; 7:1497-504.
21. Reed E. Platinum-DNA adduct, nucleotide excision repair and platinum based anti-cancer chemotherapy. Cancer Treat Rev 1998; 24:331-44.
22. Jiang H, Yang L Y. Cell cycle checkpoint abrogator UCN-01 inhibits DNA repair: association with attenuation of the interaction of XPA and ERCC1 nucleotide excision repair proteins. Cancer Res 1999; 59:4529-34.
23. Leichman C G. Thymidylate synthase as a predictor of response. Oncology (Williston Park) 1998; 12:43-47.
24. Lenz H J, Danenberg K D, Leichman C G et al. p53 and thymidylate synthase expression in untreated stage II colon cancer: associations with recurrence, survival, and site. Clin Cancer Res 1998; 4:1227-34.
25. Paradiso A, Simone G, Petroni S et al. Thymidilate synthase and p53 primary tumour expression as predictive factors for advanced colorectal cancer patients. Br J Cancer 2000; 82:560-567.
26. Watanabe T, Wu T T, Catalano P J et al. Molecular predictors of survival after adjuvant chemotherapy for colon cancer. N Engl J Med 2001; 344:1196-206.
27. Iacopetta B, Grieu F, Joseph D, Elsaleh H. A polymorphism in the enhancer region of the thymidylate synthase promoter influences the survival of colorectal cancer patients treated with 5-fluorouracil. Br J Cancer 2001; 85:827-30.
28. Takenoue T, Nagawa H, Matsuda K et al. Relation between thymidylate synthase expression and survival in colon carcinoma, and determination of appropriate application of 5-fluorouracil by immunohistochemical method. Ann Surg Oncol 2000; 7:193-98.
29. Edler D, Glimelius B, Hallstrom M et al. Thymidylate synthase expression in colorectal cancer: a prognostic and predictive marker of benefit from adjuvant fluorouracil-based chemotherapy. J Clin Oncol 2002; 20:1721-28.
30. Allegra C J, Paik S, Colangelo L H et al. Prognostic value of thymidylate synthase, Ki-67, and p53 in patients with Dukes' B and C colon cancer: a National Cancer Institute-National Surgical Adjuvant Breast and Bowel Project collaborative study. J Clin Oncol 2003; 21:241-50.
31. Chu E, Drake J C, Boarman D, Baram J, Allegra C J. Mechanism of thymidylate synthase inhibition by methotrexate in human neoplastic cell lines and normal human myeloid progenitor cells. J Biol Chem 1990; 265:8470-8478.
32. Banerjee D, Mayer-Kuckuk P, Capiaux G, Budak-Alpdogan T, Gorlick R, Bertino J R. Novel aspects of resistance to drugs targeted to dihydrofolate reductase and thymidylate synthase. Biochim Biophys Acta 2002; 1587:164-73.
33. Malet-Martino M, Jolimaitre P, Martino R. The prodrugs of 5-fluorouracil. Curr Med Chem Anticancer Agents 2002; 2:267-310.
34. Schuller J, Cassidy J, Dumont E et al. Preferential activation of capecitabine in tumor following oral administration to colorectal cancer patients. Cancer Chemother Pharmacol 2000; 45:291-97.
35. Ormrod D, Holm K, Goa K, Spencer C. Epirubicin: a review of its efficacy as adjuvant therapy and in the treatment of metastatic disease in breast cancer. Drugs Aging 1999; 15:389-416.
36. Gudkov A V, Zelnick C R, Kazarov A R et al. Isolation of genetic suppressor elements, inducing resistance to topoisomerase II-interactive cytotoxic drugs, from human topoisomerase II cDNA. Proc Natl Acad Sci USA 1993; 90:3231-35.
37. Berger J M, Gamblin S J, Harrison S C, Wang J C. Structure and mechanism of DNA topoisomerase II. Nature 1996; 379:225-32.
38. Coukell A J, Faulds D. Epirubicin. An updated review of its pharmacodynamic and pharmacokinetic properties and therapeutic efficacy in the management of breast cancer. Drugs 1997; 53:453-82.
39. GREENSPAN E M, FIEBER M, LESNICK G, EDELMAN S. Response of advanced breast carcinoma to the combination of the antimetabolite, Methotrexate, and the alkylating agent, thio-TEPA. J Mt Sinai Hosp N Y 1963; 30:246-67.
40. Cooper, R. G. Combination chemotherapy in hormone-resistant breast cancer. Proc Am Soc Cancer Res, Am Soc Clin Oncol 10, 15. 1969. Ref Type: Abstract
41. Polychemotherapy for early breast cancer: an overview of the randomised trials. Early Breast Cancer Trialists' Collaborative Group Lancet 1998; 352:930-942.
42. HEIDELBERGER C, CHAUDHURI N K, DANNEBERG P et al. Fluorinated pyrimidines, a new class of tumour-inhibitory compounds. Nature 1957; 179:663-66.
43. Fung K P, Lam W P, Choy Y M, Lee C Y. Human tumour necrosis factor-alpha inhibits glucose transport in cultured Ehrlich ascites tumour cells. Life Sci 1995; 57:L1-L6.

The invention claimed is:

1. A method for predicting the outcome of 5-FU treatment in a subject having a breast cancer, wherein said subject has not previously undergone 5-FU treatment, the method comprising the steps:
   a) determining the gene copy number of each of at least two markers from the 5-FU pathway in an isolated breast cancer sample from said subject, wherein the at least two markers are TYMS and DHFR,
   b) detecting a decreased copy number of at least one of the markers, and
   c) predicting the outcome of the 5-FU treatment in said subject based on the gene copy number levels detected, wherein a decrease in the gene copy number for either TYMS or DHFR in the breast cancer sample is predictive of breast cancer resistance to 5-FU treatment; and wherein the decrease in TYMS and DHFR gene copy number is measured with reference to at least one reference marker, wherein the at least one reference marker comprises a centromere probe.

2. The method according to claim 1, further comprising detecting a signal from at least one reference marker in the centromere region of the same chromosome as the TYMS or DHFR gene, and determining the decrease in TYMS or DHFR gene copy number based on correlation of the signal from the TYMS or DHFR gene and the signal from the at least one reference marker.

3. The method of claim 2, wherein the gene copy number is determined using probes, wherein the probes are chosen from nucleic acid probes and nucleic acid analogue probes.

4. The method of claim 2, wherein the at least one reference marker is in a centromere chosen from Cen5 and Cen18.

5. The method of claim 2 further comprising using at least one blocking probe.

* * * * *